United States Patent
Ottonello et al.

(10) Patent No.: US 10,718,070 B2
(45) Date of Patent: *Jul. 21, 2020

(54) PROCESS FOR INCREASING THE ENZYMATIC ACCESSIBILITY OF A THERMALLY TREATED LIGNO-CELLULOSIC BIOMASS FEEDSTOCK

(71) Applicant: Versalis S.p.A., San Donato Milanese (Milan) (IT)

(72) Inventors: Piero Ottonello, Milan (IT); Paolo Torre, Arenzano (IT); Stefano Paravisi, Tortona (IT); Chiara Prefumo, Genoa (IT); Pietro Pastorino, Campo Ligure (IT); Dario Giordano, Tortona (IT)

(73) Assignee: Versalis S.p.A., San Donato Milanese (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/289,956

(22) Filed: Mar. 1, 2019

(65) Prior Publication Data

US 2019/0194832 A1   Jun. 27, 2019

Related U.S. Application Data

(63) Continuation of application No. 15/032,649, filed as application No. PCT/EP2014/073428 on Oct. 31, 2014, now Pat. No. 10,233,570.

(30) Foreign Application Priority Data

Oct. 31, 2013 (IT) .............................. TO2013A0879
Oct. 31, 2013 (IT) .............................. TO2013A0880
Oct. 31, 2013 (IT) .............................. TO2013A0881
Oct. 31, 2013 (IT) .............................. TO2013A0883
Oct. 31, 2013 (IT) .............................. TO2013A0884

(51) Int. Cl.
| | |
|---|---|
| *D01G 9/14* | (2006.01) |
| *C08H 8/00* | (2010.01) |
| *C12P 19/02* | (2006.01) |
| *C12P 19/14* | (2006.01) |
| *C08B 37/00* | (2006.01) |
| *C12P 7/10* | (2006.01) |
| *C08L 97/02* | (2006.01) |

(52) U.S. Cl.
CPC ........... *D01G 9/14* (2013.01); *C08B 37/0057* (2013.01); *C08H 8/00* (2013.01); *C08L 97/02* (2013.01); *C12P 7/10* (2013.01); *C12P 19/02* (2013.01); *C12P 19/14* (2013.01); *C12P 2201/00* (2013.01); *Y02E 50/16* (2013.01)

(58) Field of Classification Search
USPC .............................................. 162/32; 19/204
See application file for complete search history.

(56) References Cited

U.S. PATENT DOCUMENTS

| | | | | |
|---|---|---|---|---|
| 5,705,216 A | * | 1/1998 | Tyson ...................... | C08H 8/00 127/37 |
| 10,233,570 B2 | * | 3/2019 | Ottonello ................ | C08H 8/00 |

* cited by examiner

*Primary Examiner* — Mark Halpern
(74) *Attorney, Agent, or Firm* — Edwin A. Sisson, Attorney at Law, LLC; Jeffrey J. Banyas

(57) ABSTRACT

It is disclosed a process for increasing the enzymatic accessibility of a thermally treated ligno-cellulosic biomass feedstock which has been thermally treated at a severity factor. The process comprises a step of fiber shives reduction, for reducing the amount of long shives. The thermally treated ligno-cellulosic biomass after fiber shives reduction is characterized by having an increased glucans accessibility and by forming a slurry having a low viscosity.

20 Claims, 12 Drawing Sheets

WELDING ENGINEERS 30 mm SCREW ARRANGEMENT for 315-4350 except as noted, screws have 30.00 mm constant pitch and 29.72mm flight O.D.

| Item # | # Required | Name | Stem - root Dia(mm) - length (mm) |
|---|---|---|---|
| 1 | 1 | Main compounder screw | cyl - 24.36 - 45.01 |
| 2 | 1 | Aux " " | cyl - 24.36 - 45.01 |
| 3 | 2 | Main Feed Screw | tapered - 19.5 to 24.36 - 157.5 |
| 4 | 2 | Aux " " | tapered - 19.5 to 24.36 - 157.5 |
| 5 | 1 | Main Mill Screw | cyl - 24.36 - 157.5 |
| 6 | 1 | Aux Mill Screw | cyl - 24.36 - 157.5 |
| 7 | 2 | Main compounder screw | cyl - 28.60 - 45.01 (no flights) |
| 8 | 2 | Aux " " | cyl - 28.60 - 45.01 (no flights) |
| 9 | 2 | Main Mill Screw | cyl - 24.36 - 112.5 |
| 10 | 2 | Aux Mill Screw | cyl - 24.36 - 112.5 |
| 11 | 1 | Main compounder screw | cyl - 28.19 - 45.01 |
| 12 | 1 | Aux " " | cyl - 28.19 - 45.01 |
| 13 | 2 | Main Mill Screw | cyl - 22.86 - 157.5 (10.01 pitch) |
| 14 | 2 | Aux " " | cyl - 22.86 - 157.5 (10.01 pitch) |
| 15 | 1 | Main Mill Screw | cyl - 22.86 - 89.84 |
| 16 | 1 | Aux " " | cyl - 22.86 - 89.84 |
| 17 | 1 | Main Mill Screw | cyl - 22.86 - 157.5 |
| 18 | 1 | Aux Extruder Screw | cyl - 22.86 - 153.6 |
| 19 | 1 | Main Extruder Screw | cyl - 24.359 - 180.4 |
| 20 | 11 | Main Connection Stud | |
| 21 | 10 | Aux " " | |

| | screw segment item #'s; from feed | screw length (mm) |
|---|---|---|
| main | 1, 3, 5, 7, 3, 9, 11, 9, 13, 13, 7, 15, 17, 19 | 1620.1 |
| aux | 2, 4, 6, 8, 4, 10, 12, 10, 14, 14, 8, 16, 18 | 1436 |

FIGURE 1

PROCESS FOR INCREASING THE ENZYMATIC ACCESSIBILITY OF A THERMALLY TREATED LIGNO-CELLULOSIC BIOMASS FEEDSTOCK

PRIORITIES AND CROSS REFERENCES

This patent application claims the priority from U.S. application Ser. No. 15/032,649 filed on 28 Apr. 2016, International Application No. PCT/EP2014/073428 filed on 31 Oct. 2014, Italian Application No. TO2013A000884 filed on 31 Oct. 2013, Italian Application No. TO2013A000879 filed on 31 Oct. 2013, Italian Application No. TO2013A000880 filed on 31 Oct. 2013, Italian Application No. TO2013A000881 filed on 31 Oct. 2013, and Italian Application No. TO2013A000883 filed on 31 Oct. 2013 the teachings of each of which are incorporated herein by reference in their entirety.

BACKGROUND

The conversion of a ligno-cellulosic biomass feedstock to bio-based chemical compounds which may be used to replace of products derived from petroleum, such as fuel and chemical raw materials, has attracted much attention over the last decades. Among conversion processes, biological conversion of sugars from ligno-cellulosic biomass feedstocks by means of enzymes and microorganisms is considered promising for producing fuels and chemicals at low cost with a very limited environmental impact.

A major difficulty in the conversion of a naturally occurring ligno-cellulosic biomass feedstock arises from the low accessibility of complex sugars, which are trapped inside the lignocellulose, a combination of lignin, hemicellulose and cellulose that strengthens biomass plant cells. Cellulose and hemicelluloses comprise respectively insoluble complex sugars, respectively C6-based glucans and C5-based xylans. A pre-treatment of the ligno-cellulosic biomass feedstock is therefore necessary to effectively disrupt the structure of the feedstock. Extensive research efforts have been devoted to various chemical pretreatments of biomass to overcome the barriers and to enhance enzyme accessibility to cellulose, by removing chemical components of biomass (lignin and/or hemicellulose).

Typically, mechanical, physical, biological and chemical pretreatments have been used.

Mechanical pretreatments are used to reduce the size of biomass feedstock and decrease the crystallinity of cellulose. Several well developed technologies are available for biomass size reduction, such as hammer milling, knife milling, shredding, and disk or attrition milling. The size reduction of biomass feedstock consumes a significant amount of electrical-mechanical energy, which is particularly critical in the case of hardwood and softwood ligno-cellulosic biomass. Typical energy consumption to produce chips with size of few centimeters is of the order of 50 Wh/kg. Depending on the process, the feedstock and the degree of milling, up to 500-700 Wh/Kg or more are needed to obtain chips of few millimeters. For most biomass resources, good sugars conversion efficiency has been achieved when pretreatment was applied to significantly size reduced biomass feedstock at the expense of consuming significant electric-mechanical energy. Therefore, even if size reduction is effective in increasing the accessibility of the sugars in the ligno-cellulosic biomass, the cost of electro-mechanical energy used in the process may be economically incompatible with the target price of the final product.

Chemical pretreatments are processes which have been adapted and tailored mainly from pulp and paper industries, wherein different chemicals are used to remove or modify key chemical components of the feedstock, thereby increasing the sugars accessibility. As the chemical agents, such as inorganic acids, bases, are extremely aggressive and environmentally dangerous, their use poses environmental concerns and add costs to waste management.

Steam explosion is another known pre-treatment technique in which the ligno-cellulosic biomass feedstock is first subjected to hydrothermal treatment at high temperature, followed by rapid release of the steam pressure to produce an explosive decompression to open up the biomass fibres. As the steam pressure is determined by the temperature, the ligno-cellulosic biomass is heated to temperature higher than 200° C., which degrade a portion of the sugars to degradation products, thereby limiting the conversion yield. Chemicals, such as acids, ammonia, sulfites are in some cases added to improve the effectiveness of the process.

A review of the pre-treatment processes may be found in Mosier et al., Bioresource Tech., 96(6):673-686, 2005.

It is known that feedstock comminution to chips before chemical pre-treatments strongly enhances the chemical impregnation of the feedstock and increases accessibility to sugars.

The use of chemical pretreatments followed by the application of mechanical forces is also disclosed. Many prior art documents disclose generic particle size reduction by means of mechanical forces after a chemical pretreatment, but they do not recognize the electro-mechanical energy consumption as the key factor limiting the real use of the combined chemical and mechanical processes. Thereby, the mechanism of fibrillation without wasting a significant portion of the electro-mechanical energy in heating the ligno-cellulosic biomass through useless friction forces has not been disclosed. Moreover, the improvement in sugars accessibility and hydrolysis yield are the only properties which are considered important to define or optimize the mechanical process. As a results, the disclosed mechanical processes are defined and conducted without taking into account important applicative properties, such as the capability of forming a low viscosity slurry.

WO2008131229A1 discloses a method of processing ligno-cellulosic material, comprising initial steam pretreatment to give pretreated ligno-cellulosic material with an average particle size, followed by refining to give refined ligno-cellulosic material with an average particle size, wherein the average particle of the pretreated ligno-cellulosic material is greater than the average particle size of the refined ligno-cellulosic material. The application discloses generic particle size reduction, without clarifying any fiberization mechanism and degree of particle size reduction.

WO2011044292 discloses a process for the thermal-mechanical pretreatment of biomass. The process includes subjecting a biomass feedstock including fibres containing cellulose, hemicellulose and lignin, to steam explosion steps and then subjecting the steam exploded biomass to axial shear forces to mechanically reduce the size of the fibres of the biomass to obtain treated biomass. The disclosed process uses a compounder comprising a shear zone, which allows the compounder to initially function as a mechanical polisher by imposing shear along the longitudinal axis of the biomass fibres in specially designed compounder screw elements. As an effect of the mechanical polishing (or fibre size reduction), enzymatic hydrolysis conversion is improved. The energy needed in the mechanical action on the fibres is quite high, as the best value presented in examples is 1.03 kWh/Kg of ligno-cellulosic biomass and a relevant amount is lost in heating by friction. Namely, a relevant amount of mechanical energy is lost in heating the biomass as it is necessary to remove the steam energy from the thermal reaction and mechanical steps. The described process also performs an important function of removing reaction degradation products, such as furfural, acetic acid, and other hydrophobic biomass extracts which are harmful or inhibitory to fermentation organisms. Thereby, the disclosed process degrades a certain amount of sugars to sugars degradation products which are then removed by flashing.

US2009298149A1 discloses a method using sulfite pretreatment to overcome recalcitrance of lignocellulose (SPORL). More specifically, it relates to a sulfite-based chemical process for pretreating biomass in solutions to reduce access barriers of enzymes to the lignocellulose, resulting in efficient conversion through enzymatic saccharification. Biomass chips or chops are directly subjected to sulfite pretreatment according to various embodiments, followed by a mechanical size reduction step (e.g., milling, abrading, grinding, crushing, chopping, chipping or the like). The application discloses a chemical pretreatment and mechanical size-reduction techniques to significantly reduce energy consumption in biomass size-reduction. Specifically, the inventors define as a target an electro-mechanical specific energy of 90 Wh/Kg to obtain a 90% of bioconversion efficiency. The solution proposed is a very aggressive chemical treatment to alter the biomass chemical and physical structure before conducting size reduction to fibres, fiber bundles, or powders. As stated in the application, the term "size-reduction process" is referred to the reduction of the wood chip to fibres and/or fibre bundles with lengths of about 2 mm.

In Chen et al., Biotechnology for Biofuels, 2012, 5:60, for increasing cellulose digestability during enzymatic hydrolysis and overall ethanol yield, a combination of low-severity sulfuric dilute acid pretreatment, deacetylation step and mechanical refining is studied. Deacetylation step in realized by NaOH impregnation in an additional deacetylation unit and mechanical refining is performed by means of a PFI mill. Mechanical refining was demonstrated to improve digestability of deacetylated and lower-severity-pretreated corn stover. The PFI mill is a laboratory-type mill, and it is essentially a compression unit, which, given the same energy input, produces refining effects differing significantly from a conventional disk refiner. Exerting force as compression rather than shear, results in higher internal fibrillation and lower external fibrillation and fibre shortening. No indication is given of the energy used in the mechanical refining, which is primarily expended on fibrillating the internal part of the single fibres.

In I. C. Hoeger et al., Cellulose (2013), 20, 807-818, two different pre-treated ligno-cellulosic biomass were subjected to mechanical fibrillation by stone grinding. Fibrillation refers to break out of fibre cell walls to produce macro or nanofibrills. Among other techniques, water retention value was used to measure the degree of fibrillation, as it is a measure of fibre swelling capacity and quantifies the amount of water in fibre pores and between fibres after elimination of free water. Thereby, it indicates the maximum amount of water which is retained by the ligno-cellulosic biomass. The water retention value increases in both the samples of the paper, indicating that the effect of the mechanical process is a fibre fibrillation.

In M. Wiman et al, Biotechnology and Bioengineering (2011), Vol. 108, n. 5, p. 1031, a comprehensive rheological characterization of dilute acid pretreated spruce followed by fibre size reduction by means of a knife mill is presented, accounting for the effects of water insoluble solids concentration, particle size distribution and the degree of enzymatic hydrolysis. The authors found that the rheological effects of particle size distribution could be attributed to the size of the fibres alone. The milling of the pretreated of the pretreated material resulted in significantly higher viscosity.

In S-H. Lee et al., Bioresource Technology 101, (2012), pag. 9645-9649, woody biomasses were pretreated with hot-compressed water and then micro/nanofibrillated by a twin-screw extruder to improve monosaccharide production yield. The authors found that partial removal of hemicellulose and lignin by the hydrothermal treatment effectively improved the fibrillation by extrusion. The extruded biomass had a fine fibrous morphology on a sub-micro/nanoscopic scale. The authors investigated electric power consumption, asserting that this is linearly decreasing on a logarithmic scale as extrusion discharge capacity increases, showing that the bigger the extruder the less the energy consumption, but they did not report the energy required to reduce the thermally pretreated woody biomass to a micro/nanofibrillated material.

SUMMARY

It is disclosed a process for increasing the enzymatic accessibility of a thermally treated ligno-cellulosic biomass feedstock which has been thermally treated at a severity factor, wherein said thermally treated ligno-cellulosic biomass comprises xylans, glucans and lignin and is in the physical forms of at least fibres, fines and fiber shives, wherein: the fibres each have a width of 75 µm or less, and a fibre length greater than or equal to 200 µm; the fines each have a width of 75 µm or less, and a fine length less than 200 µm; the fiber shives each have a shive width greater than 75 µm with a first portion of the fiber shives each having a shive length less than 737 µm and a second portion of the fiber shives each having a shive length greater than or equal to 737 µm.

The process comprises the step of fiber shives reduction, wherein the percent area of fiber shives having a shive length greater than or equal to 737 µm relative to the total area of fiber shives, fibres and fines of the thermally treated ligno-cellulosic biomass after fiber shives reduction is less than the percent area of fiber shives having a shive length greater than or equal to 737 µm relative to the total area of fiber shives, fibres and fines of the thermally treated ligno-cellulosic biomass before fiber shives reduction, wherein the percent area is measured by automated optical analysis.

It is also disclosed that a part of the fiber shives reduction may be done by separating at least a portion of the fiber shives having a shive length greater than or equal to 737 µm from the thermally treated ligno-cellulosic biomass.

It is further disclosed that a part of the fiber shives reduction may done by converting at least a portion of the fiber shives having a shive length greater than or equal to 737 µm in the thermally treated ligno-cellulosic biomass to fibres or fines.

It is also disclosed that at least a part of the fiber shives reduction may be done by applying work in a form of mechanical forces to the thermally treated ligno-cellulosic biomass, and all the work done by all the forms of mechanical forces on the thermally treated ligno-cellulosic biomass is preferably less than 500 Wh/Kg per kg of the thermally treated ligno-cellulosic biomass on a dry basis, more preferably less than 400 Wh/Kg, even more preferably less than 300 Wh/Kg, even yet more preferably less than 200 Wh/Kg, and most preferably less than 100 Wh/Kg, per kg of the thermally treated ligno-cellulosic biomass on a dry basis.

It is further disclosed that the mechanical energy applied to the thermally treated ligno-cellulosic biomass preferably is not mechanical energy derived from free-fall or gravity mixing.

It is also disclosed that the mechanical forces may be applied using a machine selected from the group consisting of single screw extruders, twin screw extruders, and banburies.

It is further disclosed that the thermally treated ligno-cellulosic biomass before fiber shives reduction may be characterized by having a viscosity of a slurry of the thermally treated ligno-cellulosic biomass before fiber shives reduction in water which is greater than the viscosity of a slurry of the thermally treated ligno-cellulosic biomass after fiber shives reduction in water, wherein the viscosities are measured at 25° C., at a shear rate of 10 s-1 and at a dry matter content of 7% by weight of each slurry.

It is also disclosed that the thermally treated ligno-cellulosic biomass after fiber shives reduction may be characterized by having a viscosity of a slurry of the thermally treated ligno-cellulosic biomass after fiber shives reduction in water less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s-1 and at a dry matter content of 7% by weight of the slurry of the thermally treated ligno-cellulosic biomass after fiber shives reduction in the water.

It is further disclosed that the percent area of the fiber shives having a shive length greater than or equal to 737 μm relative to the total area of fiber shives, fibres and fines of the thermally treated ligno-cellulosic biomass after fiber shives reduction may be less than a value selected from the group consisting of 5%, 10%, 20%, 30%, 40%, 50%, 60% and 70% of the percent area of the fiber shives having a shive length greater than or equal to 737 μm relative to the total area of fiber shives, fibres and fines of the thermally treated ligno-cellulosic biomass before fiber shives reduction.

It is also disclosed that the percent area of the fiber shives having a shive length greater than or equal to 737 μm relative to the total area of fiber shives, fibers and fines of the thermally treated ligno-cellulosic biomass before fiber shives reduction may be greater than a value selected from the group consisting of 1%, 2%, 3%, and 4%.

It is further disclosed that the percent area of the fiber shives having a shive length greater than or equal to 737 μm relative to the total area of fiber shives, fibers and fines of the thermally treated ligno-cellulosic biomass after fiber shives reduction may be less than a value selected from the group consisting of 1%, 0.5%, 0.25%, 0.2% and 0.1%.

It is also disclosed that the thermally treated ligno-cellulosic biomass may have been steam exploded as part of the thermal treatment.

It is further disclosed that the severity factor of the thermal treatment used to create the thermally treated ligno-cellulosic biomass may be less than a value selected from the group consisting of 4.0, 3.75, 3.5, 3.25, 3.0, 2.75 and 2.5.

It is also disclosed that the thermally treated ligno-cellulosic biomass after fiber shives reduction may have a first saturation humidity, and the thermally treated ligno-cellulosic biomass before fiber shives reduction has a second saturation humidity, and the first saturation humidity is less than the second saturation humidity.

It is further disclosed that the first saturation humidity may be less than a value selected from the group consisting of 20%, 30%, 40%, 50%, 60%, 70% and 80% of the second saturation humidity.

It is also disclosed that the saturation humidity of the thermally treated ligno-cellulosic biomass before fiber shives reduction may be less than a value selected from the group consisting of 6.0, 5.5, 5.0, 4.5, 4.0, 3.5, 3.0, and 2.5 g/g, expressed as gram of water per gram of thermally treated ligno-cellulosic biomass ligno-cellulosic biomass before fiber shives reduction on a dry basis.

It is further disclosed that the saturation humidity of the thermally treated ligno-cellulosic biomass after fiber shives reduction may be less than a value selected from the group consisting of 5.5, 5.0, 4.5, 4.0, 3.5, 3.0, 2.5, 2.0, 1.5, and 1.0 g/g expressed as gram of water per gram of thermally treated ligno-cellulosic biomass after fiber shives reduction on a dry basis.

It is also disclosed that the thermally treated ligno-cellulosic biomass before fiber shives reduction may have a xylose recovery greater than a value selected from the group consisting of 70%, 80%, 85%, 90%, 92%, 95%, and 98%.

It is further disclosed that the thermally treated ligno-cellulosic biomass before fiber shives reduction may have a glucose recovery greater than a value selected from the group consisting of 80%, 85%, 90%, 92%, 95%, and 98%.

It is also disclosed that the thermally treated ligno-cellulosic biomass after fiber shives reduction may have a glucans accessibility of the thermally treated ligno-cellulosic biomass after fiber shives reduction and the thermally treated ligno-cellulosic biomass has a glucans accessibility of the thermally treated ligno-cellulosic biomass before fiber shives reduction and the glucans accessibility of the thermally treated ligno-cellulosic biomass after fiber shives reduction is greater than the glucans accessibility of the thermally treated ligno-cellulosic biomass before fiber shives reduction.

It is further disclosed that the glucans accessibility of the thermally treated ligno-cellulosic biomass after fiber shives reduction may be greater than a value selected from the group consisting of 80%, 85%, 88%, 90%, 92%, 95%, and 98%.

It is also disclosed that the glucans accessibility of the thermally treated ligno-cellulosic biomass before fiber shives reduction may be less than a value selected from the group consisting of 75%, 78%, 80%, 82%, 85%, 88% and 91%.

It is further disclosed that the thermally treated ligno-cellulosic biomass before fiber shives reduction may have a dry matter content of at least 20% by weight of the total content of the thermally treated ligno-cellulosic biomass before fiber shives reduction.

It is also disclosed that the dry matter content of the thermally treated ligno-cellulosic biomass before fiber shives reduction may be the range of at least a value selected from the group consisting of 25%, 30%, 35%, and 40% by weight of the total content of the thermally treated ligno-cellulosic biomass before fiber shives reduction to less than 80% by weight of the total content of the thermally treated ligno-cellulosic biomass after fiber shives reduction.

It is further disclosed that the process may further comprise dispersing an amount of the thermally treated ligno-cellulosic biomass before, during or after fiber shives reduction into an amount of a liquid carrier comprising water to create a slurry stream.

It is also disclosed that the slurry stream may have a viscosity less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s−1 and at a dry matter content of 7% by weight of the slurry stream.

It is further disclosed that the slurry stream may have a dry matter content greater less than 100% but greater than a value selected from the group consisting of 5%, 7%, 8%, 10%, 12%, 15%, 18%, 20%, 25%, 30%, 35%, and 40%.

It is also disclosed that slurry stream may further comprises ionic groups, and that the ionic groups in the slurry stream are not derived from added mineral acids, mineral bases, organic acids, or organic bases.

BRIEF DESCRIPTION OF FIGURES

FIG. 1 is the screw design of the twin screw extruder used in the experiments.

DETAILED DESCRIPTION

Figure 2:
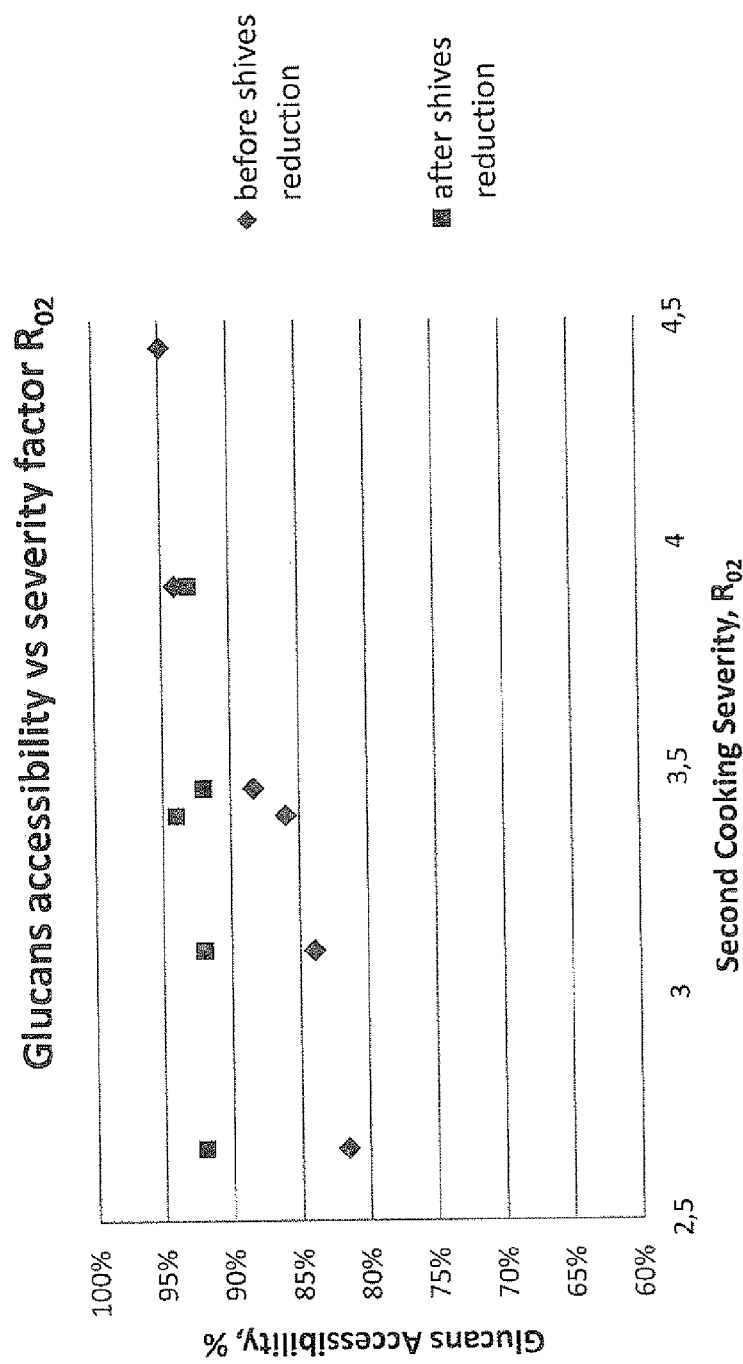
FIG. 2 depicts the glucans accessibility of thermally treated ligno-cellulosic biomass before and after fiber shives reduction at various severity factors of thermal treatment.

It is known in the paper and pulp industry that ligno-cellulosic biomass feedstocks are characterized by the content of its particles classified into fibres, fines and fiber shives. Fibres are measured on the basis of their 2 dimensional profile with fibres having a width of 75 μm or less, and a fibre length greater than or equal to 200 μm. Fines are those particles having a width of 75 μm or less, and a fines length less than 200 μm. Geometrically, one can think of a fine as a fibre which has been cut in length. Fiber shives have a shive width greater than 75 μm and can be any length. For the purpose of this specification the shive length can be categorized with a first portion of the fiber shives having a shive length less than 737 μm and a second portion of the fiber shives having a shive length in the range of greater than or equal to 737 μm. Because the width and length describe high aspect ratio particles, the width is less than the length, except in the special case of the circle or square. In the special case when the length and width equal each other the practitioner selects one measurement as the length and arbitrarily therefore, the other measurement as the width.

The 737 μm is selected on the basis of classification of the particle distribution determined by the instrument used in the experiments which gave rise to the disclosed discovery. The sizes of the particles were grouped, with one of the groups having a range of 737-1138 μm. The next group had 1138 as its minimum size. From these groups the graphs were made in figures and determinations made about the effective ranges needed to practice the discovery.

Dimensions of Common NonWood Fibres cited in the Kirk-Othmer Encyclopedia of Chemical Technology, fifth edition, are

| Fibre Source | Mean Length, μm | Mean Diameter, μm | L/D ratio |
|---|---|---|---|
| Rice straw | 1410 | 8 | 175 |
| Wheat straw | 1480 | 13 | 110 |
| Corn stalk | 1260 | 16 | 80 |
| Cotton stalk | 860 | 19 | 45 |
| Cotton liners | 3500 | 21 | 165 |
| Sugarcane bagasse | 1700 | 20 | 85 |
| Hemp | 20000 | 22 | 1000 |
| Kenaf bast | 2740 | 20 | 135 |
| Kenaf core | 600 | 30 | 20 |
| Seed flax | 27000 | 16 | 1250 |
| Bamboo | 2700 | 14 | 190 |
| Papyrus | 1500 | 12 | 125 |
| Softwood | 3000 | 30 | 100 |
| Hardwood | 1250 | 25 | 50 |

As evident, the average fibre width, as previously defined, is less than or equal to 75 μm.

It is generally viewed that the fiber shives are not a single fibre having the width greater than 75 μm, but bundle of fibres or fibre tangles which combined exhibit a width greater than 75 μm.

This invention is based upon the discovery it is the fiber shives in thermally treated ligno-cellulosic biomass which are responsible for the long enzymatic hydrolysis times, high initial viscosity of slurries from the thermally treated ligno-cellulosic biomass, and the lowered glucose recoveries and yields. This specification demonstrates that by reducing the amount (percentage) of the fiber shives in the thermally treated ligno-cellulosic biomass, the viscosity of the material in a slurry drops dramatically, and there is a significant improvement in sugar yields and recovery during fermentation.

The ability to characterize and fines, fibres and fiber shives is well known in the art and the subject of many industrial standards such as those found in the fiber characterization standards used for all the fiber characterization work in this specification.

Because fiber shives are bundles of fibres, they can be reduced in many ways. First, at least a part of the fiber shives can be removed or separated from the thermally treated ligno-cellulosic biomass. Separation techniques of fiber shives from fibres and fines is well known in the art of natural fibres (e.g. cotton, flax, and others) and also in the paper and pulp industry. Non-limiting examples are the cotton gin and wool carding apparata. Again, not limiting, the separation can occur by bulk density separation, a vibrating bed where the fiber shives separate from the fines and fibres, air elutriation, or even screening, sieving or cyclones. After separation, the fiber shives can be further processing into fibres or fines, and recombined with the thermally treated ligno-cellulosic biomass or re-fed into the thermal treatment process.

The fiber shives can also be reduced by converting them to another form. One method of converting the fiber shives is to apply mechanical forces to the thermally treated ligno-cellulosic biomass to convert the fiber shives to fibres and/or fines. An important consideration is that the difference between a fine and a fibre is the length, as both have a width of less than or equal to 75 µm. The application of mechanical forces to thermally treated ligno-cellulosic biomass is practiced in the art, but always under the belief that the fibres (less than or equal to 75 µm width) must be acted upon. By focusing the application of the mechanical forces upon the fiber shives which are bundles of fibres >75 µm, the amount of work needed is to obtain the benefits mentioned earlier is significantly less than prior art disclosures.

The reason for this reduced work requirement is analogized to yarn which is twisted fibres. It does not take much energy to pull apart a ball of tangled yarn, but it takes much more energy to actually destroy and pull apart the twisted yarn fibre.

The start of the process is the feedstock of thermally treated ligno-cellulosic biomass feedstock. The type of ligno-cellulosic biomass feedstock for the thermal treatment is covered in the feedstock selection section.

In typical conversion of ligno-cellulosic biomass feedstock to ethanol, the ligno-cellulosic biomass is thermally treated prior to enzymatic hydrolysis. Oftentimes this thermal treatment will include acids or bases to increase the liquefaction rate and reduce the hydrolysis time. In many cases the thermal pretreatment includes a steam explosion step.

The thermal treatment is measured by a severity factor which is a function the time and temperature of the thermal treatment. A preferred thermal treatment is described in the thermal treatment section of this specification.

The more time of heat exposure, the more the severe the treatment. The higher the temperature of exposure, the more the severe the treatment. The details of calculating the severity factor for this invention are described later. Steam explosion severity factor ($R_{02}$) is taken as the reference severity factor. However, conventional wisdom holds that the more severe the treatment, the more surface area and cells of the ligno-cellulosic biomass are exposed to enzymes for hydrolysis or further treatment. This is demonstrated in FIG. 2, showing that the glucans become more accessible as the severity factor increases.

Figure 3:
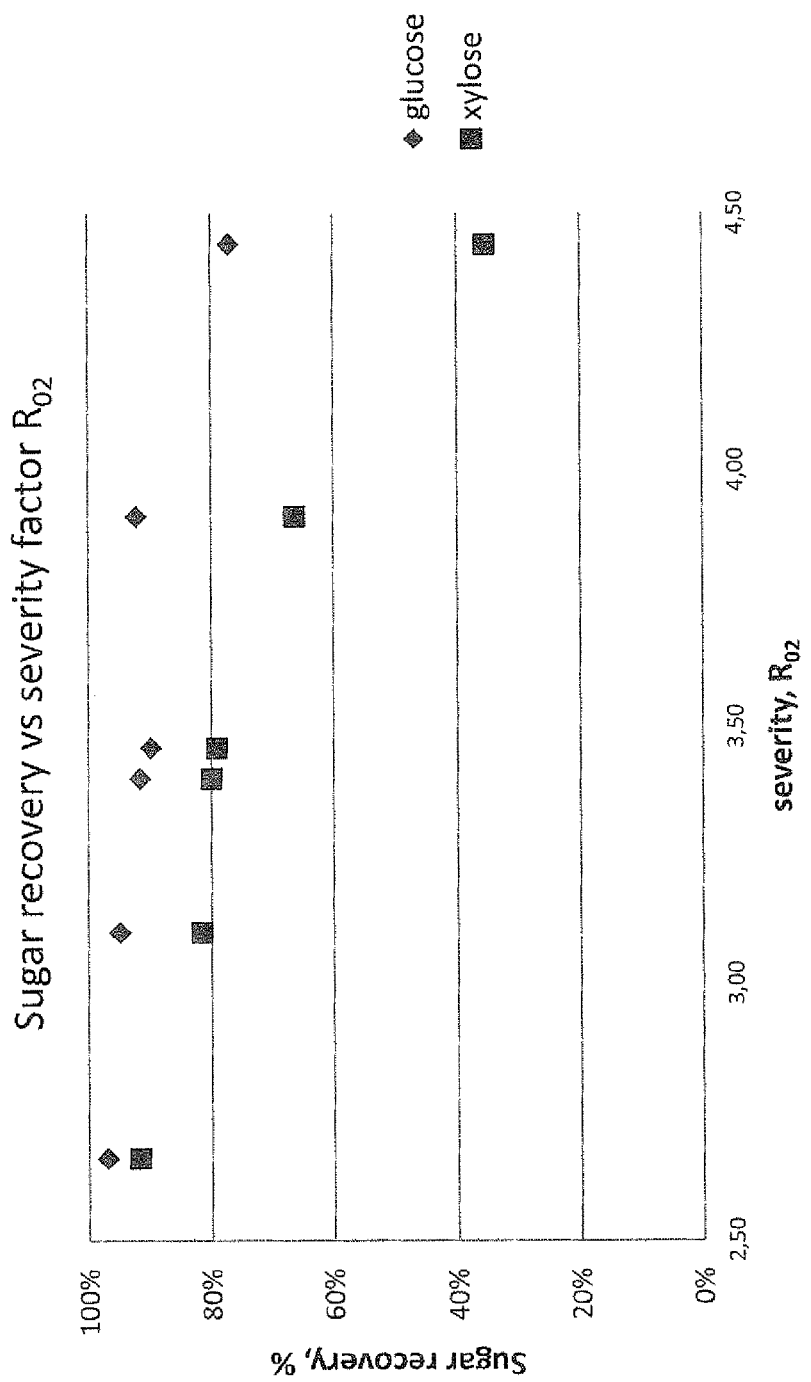
FIG. 3 depicts the glucose and xylose recovery of thermally treated ligno-cellulosic biomass at various severity factors of thermal treatment.

However, as demonstrated in FIG. 3, the amount of glucose and xylose that may be recovered relative to the amount present before the thermal treatment declines at higher severity factors. It is believed that the higher temperature converts or otherwise destroys the sugars. Thus, while the sugars existing in the thermally treated ligno-cellulosic biomass become more available, less sugars exist after severe thermal treatment because the severe temperature/time converts them to sugars degradation products, such as furfural and HMF.

Taking for example, FIG. 3, the points at severity factor 2.66, 97% of the glucose is present after the thermal treatment. In contrast, at a severity factor of 4.44 only 77% is recoverable, or alternatively 23% is destroyed. For xylose, almost 64% is destroyed. However, looking at FIG. 2, for the severity factor of 2.66, only 82% of the glucans are accessible or able to be converted to glucose. Thus, while 97% of the starting amount still exists, only 82% of that can be enzymatically converted. Looking at FIG. 2, severity factor 4.44, 95% of the glucans are accessible but remember from FIG. 3, that only 82% of the starting amount of glucans remains.

What has been discovered is that these inaccessible glucans reside in the fiber shives. When the biomass is processed it is often reduced to width and length that conform to fibres—high aspect ratio as defined in the standard. Usually the thermal treatment of the ligno-cellulosic biomass will create a thermally treated ligno-cellulosic biomass in the physical forms of at least fibres, fines and fiber shives. These physical forms are well known according the definitions described earlier.

Figure 4:
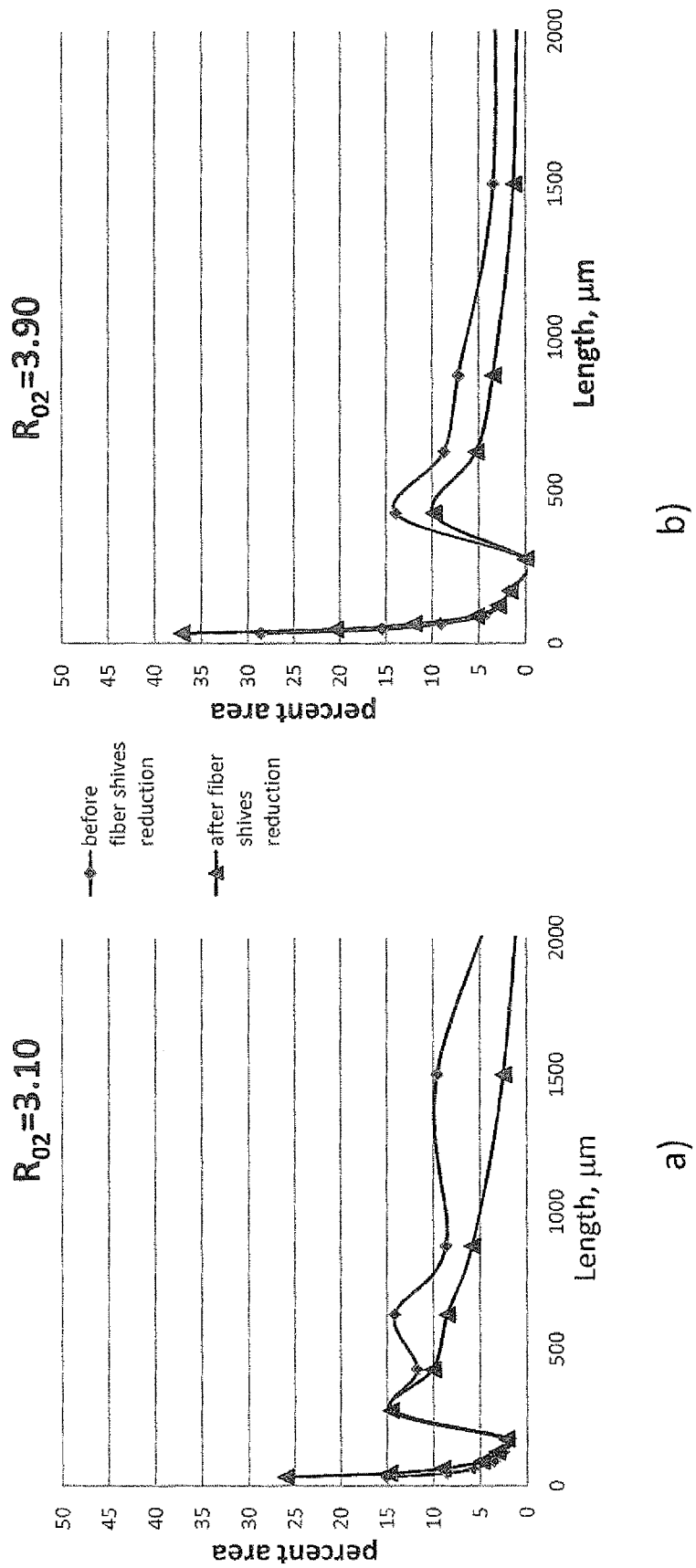
FIG. 4 is fibres and fines distribution of thermally treated ligno-cellulosic biomass before and after fiber shives reduction at two severity factors of thermal treatment.

The fines and fibres (not shives) distribution of thermally treated ligno-cellulosic biomass is shown in FIG. 4. FIG. 4a) shows the percent area of each length class relative to the total area of fines, fibres and fiber shives for the severity factor $R_{02}$ of 3.1. When the severity factor is increased to 3.91, (FIG. 4b), it is evident that the percent area of fines has increased (particles of length <200 µm) and the percent area of fibres longer than or equal to 737 µm is reduced. The same considerations hold in the case that population of fines and fibres are considered.

The plots and graphs also show the measurements of the thermally treated ligno-cellulosic biomass after fiber shives reduction, which in this case was passing it through a twin screw extruder at about 35% dry matter content having the screw element design of FIG. 1. The twin screw extruder is also known as a mechanical treatment or the application of work in the form of mechanical forces on the thermally treated ligno-cellulosic biomass. One of ordinary skill could easily obtain this design from the manufacturer listed.

The dominant role of the fiber shives is evidenced by seeing that first, according to FIG. 4, the thermally treated ligno-cellulosic biomass after fiber shives reduction through the extruder has a reduced percent area of long fibres for both the low and high severity factors of 3.1 and 3.91. However, for the low severity factor of 3.1, the conversion of fiber shives improved the glucan accessibility from 84 to 93 percent (FIG. 2). Again, the same considerations hold in the case that population of fibres and fiber shives are considered. While at the high severity of 3.91, there was substantially no improvement in the glucan accessibility. Were the long fibres responsible for accessibility, the accessibility of the glucans for the thermally treated ligno-cellulosic biomass should have been less than 94% and the reduction of the percent area of long fibres (or equivalently the population of long fibres) during the extrusion (application of mechanical forces) should have caused an increase in the accessibility. The accessibility did not increase establishing that it is not the conversion of fibres to fines that causes the increased accessibility.

Figure 5:
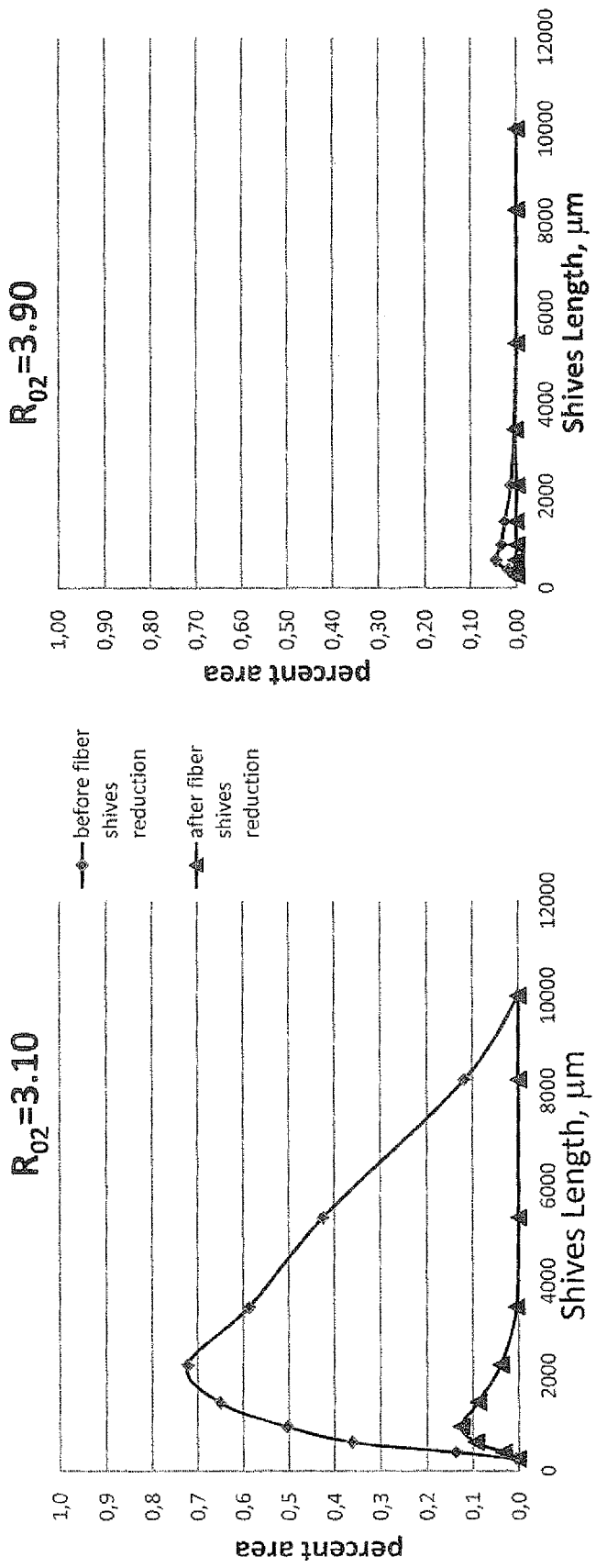
FIG. 5 is the fiber shives distribution of thermally treated biomass before shives reduction and the thermally treated biomass after shives reduction at two severity factors of thermal treatment.

The role of the fiber shives is shown in FIG. 5, which contains the percent area distribution of fiber shives of two samples prepared at low severity factor ($R_{02}$=3.10, FIG. 5a) and high severity factor ($R_{02}$=3.90, FIG. 5b), before fiber shives reduction and after fiber shives reduction. The sample at low severity before fiber shives reduction contains a remarkable amount of fiber shives and the mechanical treatment reduces the amount of fiber shives in the sample at low severity, while the sample at high severity has already a small amount of fiber shives before fiber shives reduction.

Figure 6:
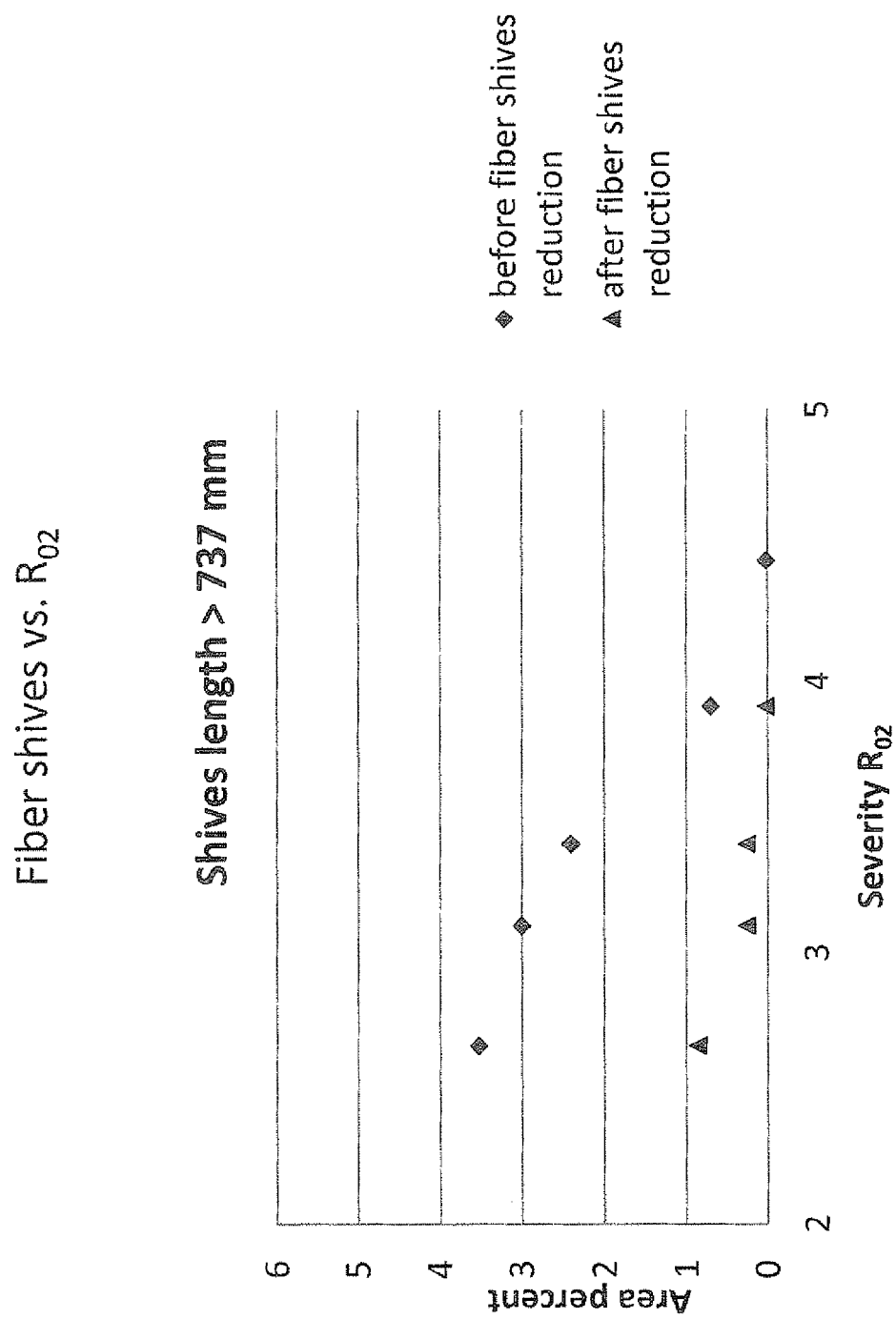
FIG. 6 is the fiber shives content of thermally treated ligno-cellulosic biomass before and after fiber shives reduction as a function of the severity factor of thermal treatment.

FIG. 6 reports the total percent area of fiber shives having a fiber shives length greater than 737 µm. The percent area of fiber shives of the sample at low severity is reduced from 3.5% to less than 1% by the fiber shives reduction. However, for the high severity thermally treated ligno-cellulosic biomass, fiber shives percent area is already less than 1% before fiber shives reduction. Thus, there is the conclusion that once the fiber shives are below a certain threshold, their removal does not impact the properties in a measurable way. Therefore, the percent area of the fiber shives having a shive length greater than or equal to 737 µm relative to the total area of fiber shives, fibres and fines of the thermally treated ligno-cellulosic biomass before fiber shives reduction is greater than a value selected from the group consisting of 1%, 2%, 3% and 4% and the percent area of the fiber shives having a shive length greater than or equal to 737 µm relative to the total area of fiber shives, fibers and fines of the thermally treated ligno-cellulosic biomass after fiber shives reduction is less than a value selected from the group consisting of 1%, 0.5, 0.25%, 0.02%, and 0.1%.

In a preferred embodiment, the percent area of the fiber shives having a shive length greater than or equal to 737 µm relative to the total area of fiber shives, fibers and fines of the thermally treated ligno-cellulosic biomass after fiber shives reduction is greater than 0, and less than a value selected from the group consisting of 1%, 0.5, 0.25%, 0.02%, and 0.1%, that is some long fiber shives are still present in the thermally treated ligno-cellulosic biomass after fiber shives reduction.

The total area of fiber shives, fibres and fines is measured using automated optical analysis which determines the area of the fiber shives, the area of the fibres and the area of fines. The proper machine, as described in the experimental section, will often provide the area of each individual class, as well as the area of each class as a percent of the total area of the sum of the classes. In the event the machine does not do the math, one of ordinary skill should be able to calculate the percent area knowing the areas, or the area knowing the total area and percent of each class measured.

In any event, the effect of the shives reduction should be such that the percent area of the fiber shives having a shive length greater than or equal to 737 µm relative to the total area of fiber shives, fibres and fines of the thermally treated ligno-cellulosic biomass after fiber shives reduction is less than a value selected from the group consisting of 5%, 10%, 20%, 30%, 40%, 50%, 60% and 70% of the percent area of the fiber shives having a shive length greater than or equal to 737 µm relative to the total area of fiber shives, fibres and fines of the thermally treated ligno-cellulosic biomass before fiber shives reduction.

Because the fiber shives are comprised of fibre bundles and agglomerated fibres, a reduced amount of energy is needed as compared to the prior art. As described in the experimental section only 0.1 to 0.2 Kw-h/kg on a wet basis or 0.25 to 0.50 Kw-h/kg on a dry matter basis was used to achieve the effects. Thus the preferred amount of work, or energy, imparted to the thermally treated ligno-cellulosic biomass is preferably less than a number selected from the group consisting of 500 Wh/Kg, 400 Wh/Kg, 300 Wh/Kg, 200 Wh/Kg, 100 Wh/Kg, per kg of the thermally treated ligno-cellulosic biomass on a dry basis. It is preferable that at least a part of the fiber shives reduction is done by applying mechanical forces to the thermally treated ligno-cellulosic biomass, and all the work applied in form of mechanical forces on the thermally treated ligno-cellulosic biomass is less than 500 Wh/Kg per kg of the thermally treated ligno-cellulosic biomass on a dry basis. It is even more preferable that all the work done by all the forms of mechanical forces on the thermally treated ligno-cellulosic biomass is less than a value selected from the group consisting of 400 Wh/Kg, 300 Wh/Kg, 200 Wh/Kg, 100 Wh/Kg, per kg of the thermally treated ligno-cellulosic biomass on a dry basis.

The application of mechanical forces to the thermally treated ligno-cellulosic biomass should be a mechanical process or sub-processes which applies work to the thermally treated ligno-cellulosic biomass and reduces the number of fiber shives longer than or equal to 737 µm during the fiber shives reduction. Mechanical forces applying work are distinct from chemical processes which may dissolve the fiber shives, for example. The type of forces or work applied as a mechanical force is shear, compression, and moving. It should be appreciated that the mechanical treatment may be a conversion process where the application of mechanical forces converts at least a portion of the fiber shives in the thermally treated ligno-cellulosic biomass to fibres or fines that remain part of the output. One class of machines for applying this type of work in a mechanical manner are those machines which apply shear such as an extruder, a twin screw extruder, a co-rotating extruder, a counter-rotating twin screw extruder, a disk mill, a bunbury, a grinder, a rolling mill, a hammer mill.

Preferably, the mechanical energy applied to the thermally treated ligno-cellulosic biomass is not mechanical energy derived from free-fall or gravity mixing.

In any case, it is noted the amount of work applied to the thermally treated ligno-cellulosic biomass for a given amount of time should be greater than the amount of work that can be provided by the forces of gravity or free fall mixing in that same period. One way to measure this is to consider the period of time in which the fiber shives are reduced to be the called fiber shives reduction time. The amount of work applied to the thermally treated ligno-cellulosic biomass during the fiber shives reduction time is preferably greater than the amount of work which can be applied to the thermally treated ligno-cellulosic biomass by free fall mixing or gravity. One embodiment will have no work applied in the form of free fall mixing or gravity during the shives reduction.

The fiber shives reduction time is preferably in the range of 0.1 to 30 minutes. While the fiber shives reduction time can be any positive amount less than 12 hours, less than 6 hours is more preferable, with less than 3 hours even more preferred and less than 1 hour more preferred, and less than 30 minutes being more preferable with less than 20 minutes being most preferred. In the case of an extruder, the preferred fiber shives reduction time is in the range of 0.1 to 15 minutes.

One of ordinary skill knowing that the forces are to be applied to fibre shives which on the average are 2 to 5 times the width of the fibre (less than or equal to 75 µm, averaging of 30-40 µm versus the fiber shives of 130-180 µm width) can easily adjust the apparatus. The twin screw extruder applies mechanical work in the forms of shear, compression and movement down the barrel of the screw. For a twin screw extruder one keeps the flights and distances further apart, as tighter distances applying forces to fibres are only wasted. In the experiments conducted in this specification, a conventional twin screw extruder for PET resins was used with no special screw as described in the prior art. For mills or blades, one sets the distance between the two parts creating the force for the particles having width of 130-180 µm, not the particles less than or equal to 75 µm.

The simplest example of these machines are grist mills where two stones are rotated with a space between them. The space between the stones sets the size. One of ordinary skill would set the stones a distance apart to apply the force to particles having a width of >75 with the fibres having a width of less than 75 µm passing between the stones with little or no work applied to these smaller particles. A disk mill is of the similar operation as it is the space between the disks which sets the application of the force.

Figure 7:
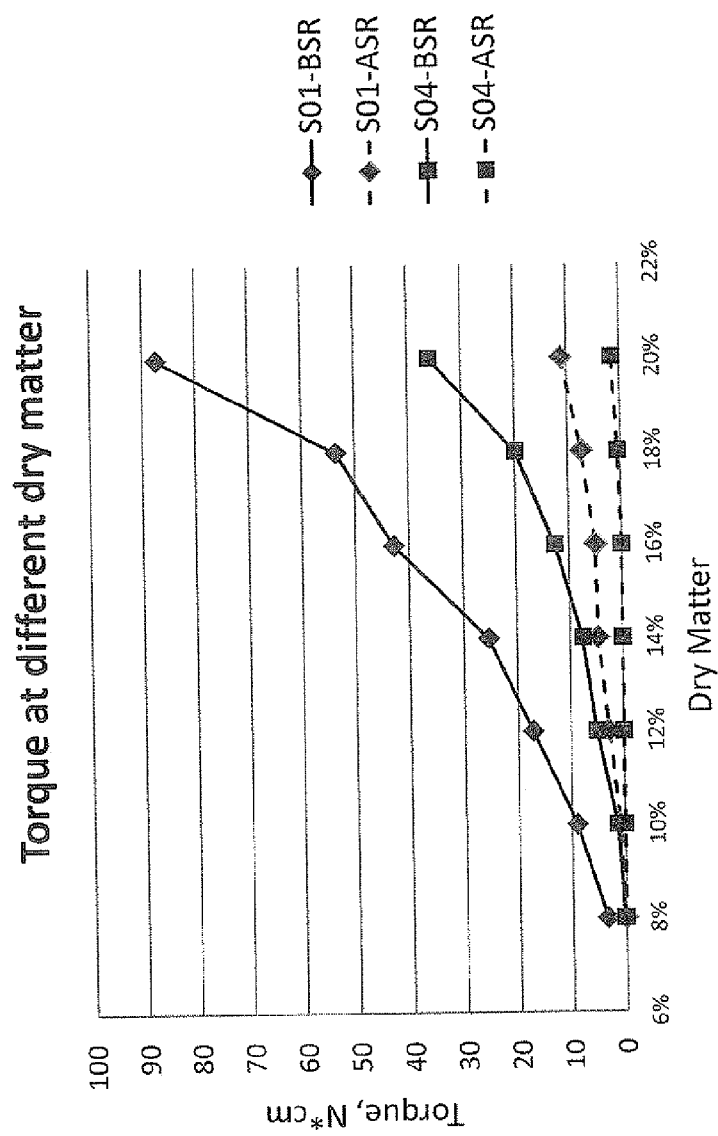
FIG. 7 plots the torque of slurries of various experimental runs at different dry matter contents in the slurry.

An additional feature it has been discovered, that once the fiber shives level is low enough, the thermally treated ligno-cellulosic biomass after fiber shives reduction will have much lower viscosity than the thermally treated ligno-cellulosic biomass when both are made into a slurry of water at the same dry matter content. FIG. 7 demonstrates this, at 20% dry matter the S01 (produced at a steam explosion severity factor of 2.66)) thermally treated material before fiber shives reduction needed a torque of 87 N-cm, while the thermally treated ligno-cellulosic biomass after shives reduction, needed only 11 N-cm.

Figure 8:
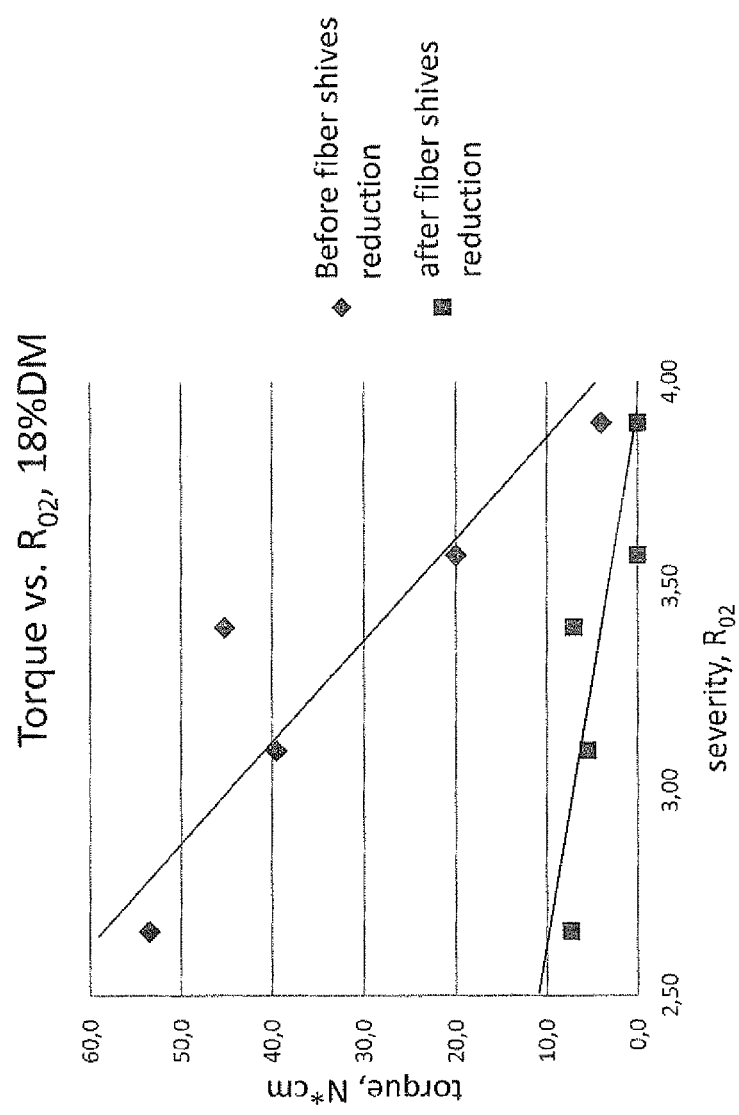
FIG. 8 plots the torque of slurries made from 18% dry matter content of the thermally treated ligno-cellulosic biomass before and after fiber shives reduction as a function of the severity factor of thermal treatment.

FIG. 8 shows the torque needed to agitate a slurry at 18% dry matter of thermally treated materials prepared at different severity factor, before and after fiber shives reduction. The torque decreases by increasing the severity factor, as the samples at low severity factor contain a bigger amount of fiber shives (FIG. 6). For each thermally treated material, the torque decreases by reducing the fiber shives by means of a mechanical treatment, but the effect is remarkably more evident in samples at low severity factor, which contains more fiber shives.

This slurry effect is especially critical as it can be can be done without hydrolysis, meaning that the low viscosity stream can be passed over an immobilized enzyme bed for enzymatic hydrolysis, or passed over a ion exchange resin for cationic exchange and subsequent "acid" hydrolysis.

Figure 10:
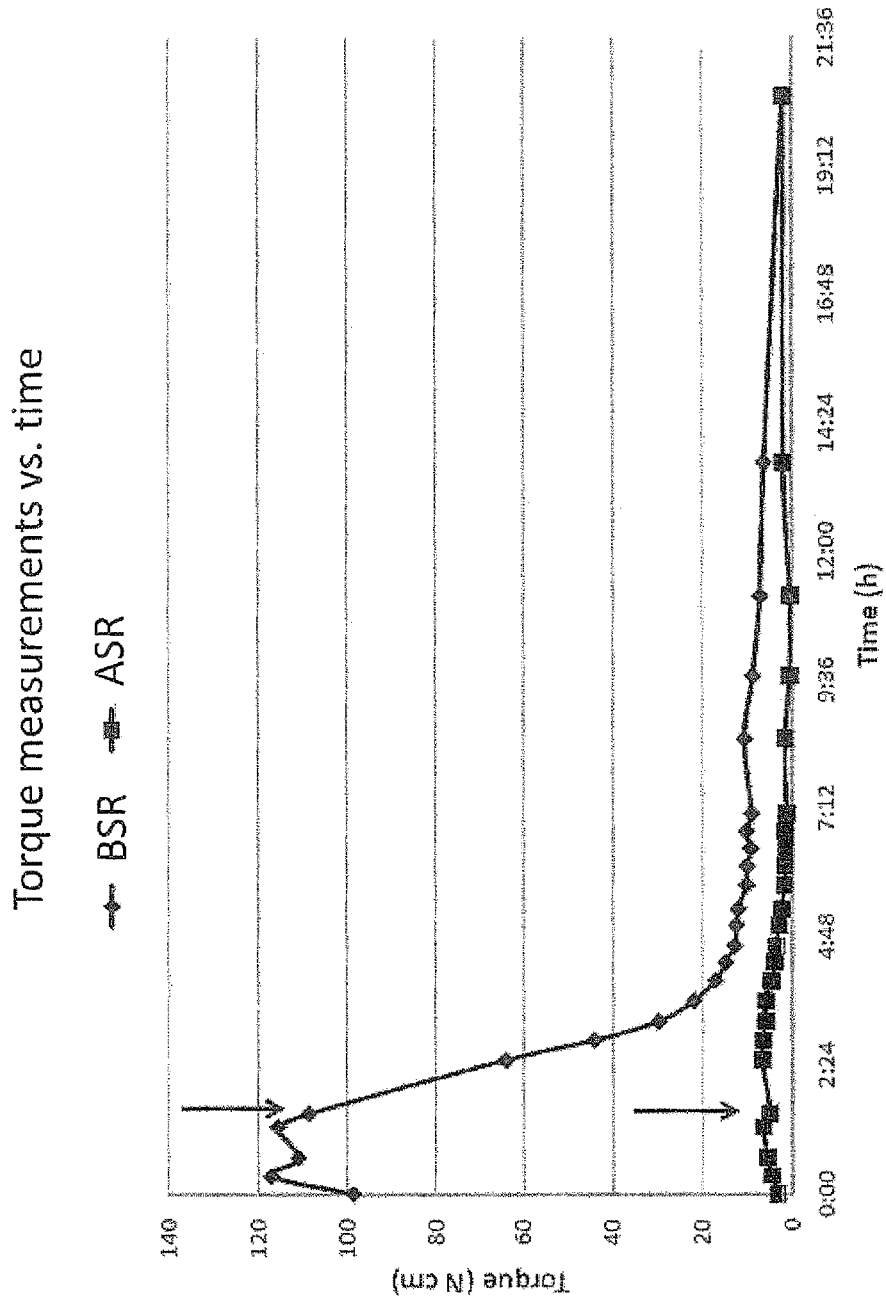
FIG. 10 plots the torque measurement versus time of thermally treated ligno-cellulosic biomass before and after fiber shives reduction.

This property is especially useful when exposing the material to enzymatic hydrolysis. In FIG. 10, the thermally treated ligno-cellulosic biomass before fiber shives reduction and the thermally treated ligno-cellulosic biomass after shives reduction were "slurried" into water with enzymes added at the arrow. It took 2+ hours after the enzymes were added for the viscosity of the thermally treated ligno-cellulosic biomass before fiber shives reduction to approach that of the thermally treated ligno-cellulosic biomass after fiber shives reduction. Thus, the process can be further characterized in that the output of thermally treated ligno-cellulosic biomass after fiber shives reduction is characterized by having a viscosity of a slurry of the thermally treated ligno-cellulosic biomass after fiber shives reduction in water less than the viscosity of a slurry of the thermally treated ligno-cellulosic biomass before fiber shives reduction in water, wherein the viscosities are measured at 25° C., at a shear rate of 10 s$^{-1}$ and at a dry matter content of 7% by weight of each slurry.

The process can be further characterized in that the thermally treated ligno-cellulosic biomass after fiber shives reduction is characterized by having a viscosity of a slurry of the thermally treated ligno-cellulosic biomass after fiber shives reduction in water less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s$^{-1}$ and at a dry matter content of 7% by weight of the slurry of the thermally treated ligno-cellulosic biomass after fiber shives reduction in the water.

The process can further comprise a slurry step, wherein the thermally treated ligno-cellulosic biomass before, during or after fiber shives reduction is dispersed into a liquid carrier, preferably comprising water or aqueous, to create a slurry stream. The slurry stream preferably has a viscosity less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s$^{-1}$ and at a dry matter content of 7% by weight of the slurry stream. The slurry stream will preferably have a dry matter content less than 100% but greater than a value selected from the group consisting of 5%, 7%, 8%, 10%, 12%, 15%, 18%, 20%, 25%, 30%, 35%, and 40%.

Because this slurry stream having this viscosity can be made without the use of hydrolysis catalysts such as enzymes, acids or bases, thus, the inventors have discovered an entirely new article of manufacture which is a slurry comprising water, soluble sugars, solid lignin, solid cellulose, which has a dry matter content in the range of 20 to 80% by weight of the total amount of the slurry and is void of or substantially void of a hydrolytic catalyst such as an enzyme or enzymes. Other preferable ranges of dry matter range are 25 to 80% by weight, with 30 to 80% by weight even more preferable. In some instances the dry matter range will have an upper limit of 70% by weight, with 60% less preferable and 40% even less preferable.

The torque of the slurry comprising the thermally ligno-cellulosic biomass after fiber shives reduction at 10 minutes after the addition of the solvent is less than the torque of a mixture of the thermally treated ligno-cellulosic biomass before fiber shives reduction when using the same amount and composition of the solvent measured 10 minutes after the solvent has been added to the thermally pre-treated ligno-cellulosic biomass before fiber shives reduction and under the same mixing condition when both torque measurements are at 25° C. Preferably the torque of the thermally treated ligno-cellulosic biomass after fiber shives reduction should be at least less than 50% of the torque of the thermally treated ligno-cellulosic biomass before fiber shives reduction, with at least less than 40% even more preferred, with at least less than 30% even more preferred.

It is also preferable that the solvent creating the slurry is not pure recycled process water as offered in WO 2011/044292 and WO 2011/044282, but to use liquid containing solubles and possibly insolubles from a hydrolysis reactor or alternatively use materials derived from the stillage after the hydrolyzed material has been fermented. In another embodiment, the solvent comprises liquids produced during the thermal treatment, said liquids comprising monomeric and oligomeric sugars which have been solubilized as an effect of the thermal treatment. While the addition point in WO 2011/044292 and WO 2011/044282 is at the end of a compounder, the liquid comprising the hydrolysis products of a similarly, if not same, ligno-cellulosic biomass, also considered a solvent in this specification is used to slurry the thermally treated ligno-cellulosic biomass after fiber shives reduction.

The thermally treated ligno-cellulosic biomass, either before and after fiber shives reduction, comprises glucans, xylans and lignin. As the thermal treatment is preferably conducted so as to avoid the removal of all or great amount of the lignin of the starting ligno-cellulosic biomass feedstock, the percent lignin content of the thermally pretreated ligno-cellulosic biomass is greater than 15% by weight on a dry basis. Depending on the feedstock selection and the specific thermal pretreatment, the percent lignin content of the thermally pretreated ligno-cellulosic biomass may be greater than 20%, preferably greater than 25%, more preferably greater than 30%, even more preferably greater than 40%, and most preferably greater than 50%.

The thermally treated ligno-cellulosic biomass, either before and after fiber shive reduction may be further characterized by the ratio of the amount by weight of glucans of the thermally treated ligno-cellulosic biomass to the amount of lignin of the thermally treated ligno-cellulosic biomass, which may be greater than a value selected from the group consisting of 1.5, 1.8, 2.0, 2.2, and 2.5.

Figure 9:
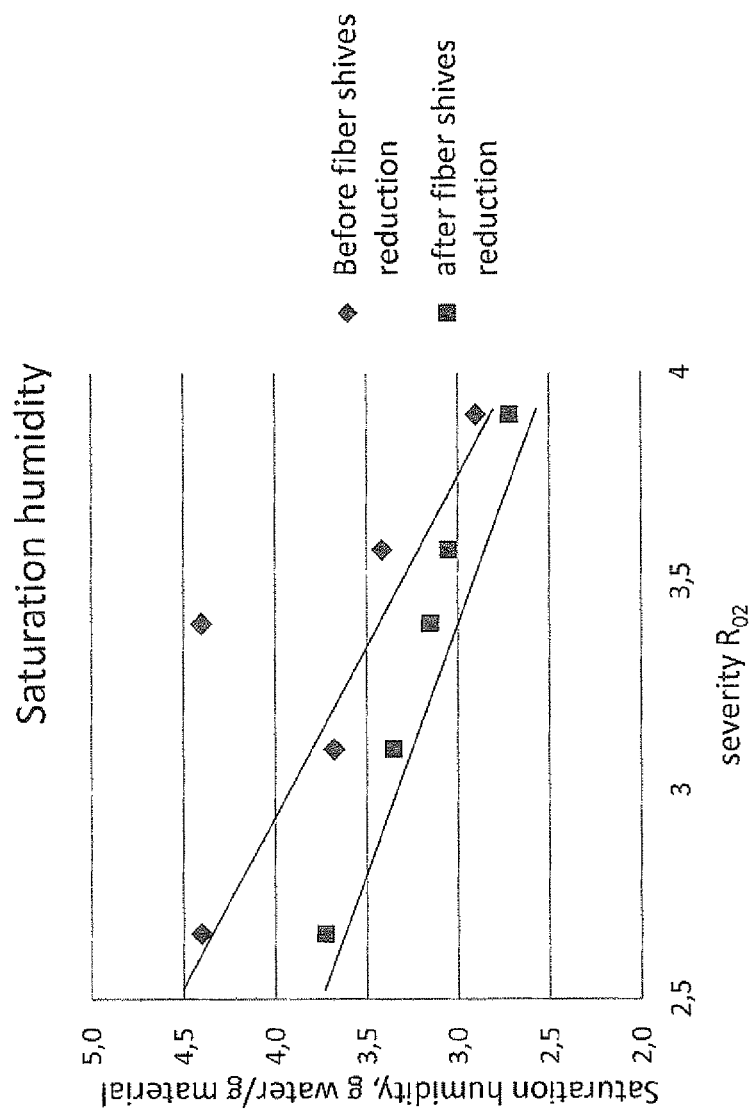
FIG. 9 plots the saturation humidity of thermally treated ligno-cellulosic biomass before and after fiber shives reduction at different severity factors of thermal treatment.

The process can be further characterized, as demonstrated in FIG. 9, by the saturation humidity of the thermally treated ligno-cellulosic biomass after fiber shives reduction and the thermally treated ligno-cellulosic biomass before fiber shives reduction because the saturation humidity of the thermally treated ligno-cellulosic biomass after fiber shives reduction is less than the saturation humidity of thermally treated ligno-cellulosic biomass.

It can be said that thermally treated ligno-cellulosic biomass after fiber shives reduction has a first saturation humidity, and the thermally treated ligno-cellulosic biomass before fiber shives reduction has a second saturation humidity, and the first saturation humidity is less than the second saturation humidity.

In fact, when compared to each other the saturation humidity of the thermally treated ligno-cellulosic biomass after fiber shives reduction is less than a value selected from the group consisting of 20%, 30%, 40%, 50%, 60%, 70% and 80% of the thermally treated ligno-cellulosic biomass before fiber shives reduction.

In terms of output characterization, the saturation humidity of the thermally treated ligno-cellulosic biomass after fiber shives reduction is preferably less than a value selected from the group consisting of 5.5, 5.0, 4.5, 4.0, 3.5, 3.0, 2.5, 2.0, 1.5, and 1.0 g/g expressed as gram of water per gram of thermally treated ligno-cellulosic biomass after fiber shives reduction on a dry basis.

In terms of feedstock selection it is preferable that the saturation humidity of the thermally treated ligno-cellulosic biomass before fiber shives reduction is less than a value selected from the group consisting of 6.0, 5.5, 5.0, 4.5, 4.0, 3.5, 3.0, and 2.5 g/g, expressed as gram of water per gram of thermally treated ligno-cellulosic biomass ligno-cellulosic biomass on a dry basis.

The thermally treated ligno-cellulosic biomass preferably has a dry matter content of at least 20% by weight of the total content of the thermally treated ligno-cellulosic biomass. With the dry matter content of the thermally treated ligno-cellulosic biomass preferably in the range of at least a value selected from the group consisting of 25%, 30%, 35%, and 40% by weight of the total content of the thermally treated ligno-cellulosic biomass to less than 80% by weight of the total content of the thermally treated ligno-cellulosic biomass.

Xylose recovery is the percent ratio between the total amount of xylans in the thermally treated ligno-cellulosic biomass before fiber shives reduction (as xylose equivalents calculated including insoluble xylans, xylo-oligomers, xilobiose and xylose present in both the solid and liquid of the ligno-cellulosic biomass) and the total amount of xylans (converted in xylose equivalents) present in the raw material before the thermal treatment. The complementary to 100% of the xylose recovery represents therefore the total amount of xylans degradation products as an effect of the thermal treatment.

In the case when the fiber shives reduction converts fiber shives to fines or fibres, the amount of xylose equivalents in the final composition after fiber shives reduction is the same as the amount of xylose equivalents in the thermally treated material before fiber shives reduction.

In terms of xylose recovery, the thermally treated ligno-cellulosic biomass before fiber shives reduction may preferably have a xylose recovery greater than a value selected from the group consisting of 85%, 90%, 92%, 95%, and 98%.

Glucose recovery is the percent ratio between the total amount of glucans in the thermally treated ligno-cellulosic biomass before fiber shives reduction (as glucose equivalents calculated including insoluble glucans, gluco-oligomers, cellobiose and glucose present in both the solid and liquid of the ligno-cellulosic biomass) and the total amount of glucans (converted in glucose equivalents) present in the raw material before the thermal treatment. The complementary to 100% of the glucose recovery represents therefore the total amount of glucans degradation products as an effect of the thermal treatment.

In terms of glucose recovery, the thermally treated ligno-cellulosic biomass before fiber shives reduction preferably has a glucose recovery greater than a value selected from the group consisting of 90%, 92%, 95%, and 98%. The glucans accessibility of the thermally treated ligno-cellulosic biomass before fiber shives reduction is preferably greater than a value selected from the group consisting of 80%, 85%, 88%, 90%, 92%, 95%, and 98% or the glucans accessibility can be lower than a value selected from the group consisting of 75%, 78%, 80%, 82%, 85%, 88% and 91%.

Like xylose, in the case when the fiber shives reduction converts fiber shives to fines or fibres, the amount of glucose equivalents in the final composition after fiber shives reduction is the same as the amount of glucose equivalents in the thermally treated material before fiber shives reduction.

In terms of glucans accessibility, the thermally treated ligno-cellulosic biomass after fiber shives reduction has a first glucans accessibility and the thermally treated ligno-cellulosic biomass before fiber shives reduction has a second glucans accessibility and the first glucans accessibility is greater than the second glucans accessibility.

As the experiments in this specification were done without the addition of acids or bases, it can be said that the thermally treated ligno-cellulosic biomass may preferably be free of added ionic species such as acids or bases, which are species added to the thermally treated ligno-cellulosic biomass after harvesting, i.e. not part of its natural composition. Thus the thermally treated ligno-cellulosic biomass is free of an added acid and/or added base. It is preferred then that if there any ionic groups that the amount and type of ionic groups present in the ligno-cellulosic feedstock are the amounts and types of the respective ionic groups that are not derived from the group consisting of mineral acids, organic acids and organic bases, in particular those mineral acids, organic acids and organic bases which have been added to the thermally treated ligno-cellulosic biomass after harvesting.

The same is true of the process itself of thermal treatment and mechanical treatment as these steps can be conducted in the absence of an added acid and/or added base.

In particular, preferably the thermally treated ligno-cellulosic biomass does not contain sulfur. In the case that sulfur is already present in the ligno-cellulosic biomass feedstock, the percent amount of sulfur by weight in the thermally pretreated ligno-cellulosic biomass on a dry basis is preferably less than a value selected from the group consisting of 4%, 3%, 2, and 1%.

The thermal treatment preferably have a severity ($R_O$) lower than a value selected from the group consisting of 4.0, 3.75, 3.5, 3.25, 3.0, 2.75 and 2.5. The preferred thermal treatment will also comprise a steam explosion step.

In a preferred embodiment, the thermal treatment is conducted at low severity factor, so as to enhance the fiber shives reduction effects in the thermally treated ligno-cellulosic material after fiber shives reduction with respect to the thermally treated ligno-cellulosic biomass before fiber shives reduction. Moreover, the low severity thermal treatment will be more convenient, as it requires less thermal energy. As a consequence the low severity thermally treated ligno-cellulosic biomass after fiber shives reduction will have some peculiar properties.

It is known in the art that a severe thermal treatment has a more remarkable effect on xylans, in terms of solubilization and/or degradation, than on glucans. Thereby, the low severity thermally treated ligno-cellulosic biomass will contain more xylans, with respect to glucans, than a high severity thermally treated ligno-cellulosic biomass, as evident in FIG. 3. This is evident in the graph of FIG. 3. The fiber shives reduction step is conducted substantially to not change the chemical composition of the thermally treated ligno-cellulosic biomass, thereby the thermally treated ligno-cellulosic biomass, either before and after fiber shives reduction, may be characterized by having a percent ratio of the amount of xylans to the amount of glucans which is greater than 5%, more preferably greater than 10%, even more preferably greater than 15%, even more preferably greater than 20%, even yet more preferably greater than 25%, and most preferably greater than 30%. On the other hand, less xylans and glucans degradation product, such as furfural and HMF, will be generated in the thermal treatment.

It is also known in the art that by increasing the severity factor of the thermal treatment, lignin is subjected to a depolimerization process, due to the breakage if internal bonds, and to a repolimerization, or condensation, process.

Thereby, as the ligno-cellulosic biomass is treated preferably at low severity, the thermally treated ligno-cellulosic biomass after fiber shives reduction may be further characterized by having unique properties of the lignin in the composition. Preferably, the thermal treatment is conducted to avoid, or limit, condensation effects.

Lignin is a complex network formed by polymerisation of phenyl propane units and it constitutes the most abundant non-polysaccharide fraction in lignocellulose. The three main monomers in lignin are p-coumaryl alcohol, coniferyl alcohol and sinapyl alcohol, and they are most frequently joined through arylglyceryl-B-aryl ether bonds (indicated as β-O-4). Lignin is linked to hemicellulose and embeds the carbohydrates thereby offering protection against microbial and chemical degradation.

The three monomers are polymerized in three basic polymeric units, guaiacyl (G) units from the precursor trans-coniferyl-alcohol, syringyl (S) units from the precursor sinapyl alcohol and p-hydroxyphenyl (H) units from the precursor sinapyl alcohol. Lignin is usually characterized in terms of the ratio between these units, particular by the ratio S/G.

Specific ranges of lignin properties may be defined at least in the groups of softwoods, hardwoods and agricultural grasses.

Thereby, the lignin of the low severity thermally treated ligno-cellulosic biomass after fiber shives reduction may be further characterized by specific ranges of β-O-4 bonds, depending on the severity factor of the thermal treatment. β-O-4 bonds may be measured by means of $^{13}C$-$^{1}H$ 2D HSQC NMR technique according to the protocol reported in J. Li et al, Bioresource Technology 98 (2007), p-3061-3068. The percent amount of β-O-4 bonds, expressed as number of β-O-4 bonds per 100 phenyl propane units may be greater than a value selected from the group consisting of 10%, 20%, 25%, 30%, 35%, 40%, 45% and 50%.

The molar concentration of β-O-4 bonds may be expressed also as amount of mmol of β-O-4 bonds per gram of solid composition on a dry basis, as determined by means of $^{31}P$ NMR, which may be greater than a value selected from the group consisting of 0.3 mmol, 0.5 mmol, 0.8 mmol, 1.0 mmol, 1.2 mmol, and 1.5 mmol per gram of the solid composition on a dry basis.

The lignin of the low severity thermally treated ligno-cellulosic biomass after fiber shives reduction may be further characterized by having a aliphatic hydroxyl content which is greater than 1 mmol, 1.5 mmol, 2 mmol, 2.5 mmol, 3 mmol, 3.5 mmol, and 4 mmol per gram of solid composition on a dry basis.

The lignin of the low severity thermally treated ligno-cellulosic biomass after fiber shives reduction may be further characterized by the ratio S/G of syringyl units to guaiacyl units as determined by $^{31}P$ NMR. The ratio S/G may be less than a value selected from the group consisting of 2.5, 2, 1.8, 1.5, 1.2, 1.0, and 0.8.

Low Viscosity Slurry

The formation of a slurry requires the dispersion of the thermally treated ligno-cellulosic biomass in a liquid carrier, wherein the dispersion may occur before, during or after the fiber shives reduction step.

In an embodiment, the carrier liquid is added to the thermally treated ligno-cellulosic biomass after fiber shives reduction.

In another embodiment, is the thermally treated ligno-cellulosic biomass after fiber shives reduction to be added to the carrier liquid.

In another embodiment, is the thermally treated ligno-cellulosic biomass before or during fiber shives reduction to be added to the carrier liquid, and then subjected to fiber shives reduction, for instance by means of a disk refiner or an apparatus to remove shives.

In yet another embodiment, the carrier liquid is added to the thermally treated ligno-cellulosic biomass before or during fiber shives reduction.

Mixing may be applied to promote the dispersion of the treated biomass in the liquid carrier.

In preferred embodiment, the treated biomass is inserted in a vessel and a carrier liquid comprised of water is added to reach a desired dry matter content by weight in the mixture. Liquid may be added, partly or in its entirety, before the insertion into the vessel. Added liquid may be added before or during mixing. Added liquid is preferably added in a continuous way. In one embodiment, the final dry matter in the mixture is 15% by weight or greater and described in further detail below.

In one embodiment, the added liquid carrier comprises water. The added liquid carrier may comprise liquids produced from the thermal treatment of the ligno-cellulosic biomass feedstock, wherein said liquids eventually comprises also undissolved particles of the feedstock. In one embodiment, the added carrier liquid may also comprise dissolved sugars from the thermally treated biomass before or after fiber shives reduction. In another embodiment, the carrier liquid may also comprise soluble species obtainable from either a previously liquefied slurry of the treated ligno-cellulosic biomass after fiber shives reduction or the hydrolysis of the treated ligno-cellulosic biomass after fiber shives reduction. The carrier liquid may or may not contain a hydrolysis catalyst such as an enzyme which hydrolyses the cellulose into glucose In various embodiment, additives may be present in the carrier liquid. Preferably, low shear mixing condition are applied to the mixture, for instance by means of a Rushton impeller. A person skilled in the art knows how to properly apply a low shear to a mixture, by selecting setup and mixing parameters.

As stated previously, the inventors surprisingly discovered that once the carrier liquid contacts the thermally treated ligno-cellulosic biomass after fiber shives reduction, the dispersion of the thermally treated ligno-cellulosic biomass into the carrier liquid proceeds quickly. This is immediately seen by comparing the torque applied to a stirrer disposed in the produced slurry, described as the applied torque, with the applied torque of thermally ligno-cellulosic biomass which has not been subjected to fiber shives reduction, which has also been combined with the carrier liquid, at the same dry weight percent.

Enzymatic Hydrolysis

After creation of the slurry, the slurry may be subjected to a catalyst composition, as described more fully below. It is in other words desirable to subject polysaccharide-containing biomasses to enzymatic hydrolysis in order to be able to subsequently produce bio-ethanol-containing fermentation broths suitable for distillation of ethanol.

As indicated above, the slurry containing the mechanically thermally treated lingo-cellulose can be subjected to enzymatic hydrolysis. The three major constituents in plant biomass are cellulose, hemicellulose and lignin, which are commonly referred to by the generic term lignocellulose.

Cellulose, hemicellulose and lignin are present in varying amounts in different plants and in the different parts of the plant and they are intimately associated to form the structural framework of the plant.

Cellulose is a homopolysaccharide composed entirely of D-glucose linked together by β-1,4-glucosidic bonds and with a degree of polymerisation up to 10,000. The linear structure of cellulose enables the formation of both intra- and intermolecular hydrogen bonds, which results in the aggregation of cellulose chains into micro fibrils. Regions within the micro fibrils with high order are termed crystalline and less ordered regions are termed amorphous. The micro fibrils assemble into fibrils, which then form the cellulose fibres. The partly crystalline structure of cellulose along with the microfibrillar arrangement, gives cellulose high tensile strength, it makes cellulose insoluble in most solvents, and it is partly responsible for the resistance of cellulose against microbial degradation, i.e. enzymatic hydrolysis.

Hemicellulose is a complex heterogeneous polysaccharide composed of a number of monomer residues: D-glucose, D-galactose, D-mannose, D-xylose, L-arabinose, D-glucuronic acid and 4-O-methyl-D-glucuronic acid. Hemicellulose has a degree of polymerisation below 200, has side chains and may be acetylated. In softwood like fir, pine and spruce, galactoglucomaunan and arabino-4-methyl-glucuronoxylan are the major hemicellulose fractions. In hardwood like birch, poplar, aspen or oak, 4-O-acetyl-4-methyl-glucuronoxylan and glucomaunan are the main constituents of hemicellulose. Grasses like rice, wheat, oat and switch grass have hemicellulose composed of mainly glucuronoarabinoxylan.

Bio-ethanol production from polysaccharide containing biomasses can be divided into three steps: 1) pretreatment 2) hydrolysis of the polysaccharides into fermentable carbohydrates 3) and fermentation of the carbohydrates.

Following the treatment, the next step in utilization of polysaccharide containing biomasses for production of bio-ethanol or other biochemicals is hydrolysis of the liberated starch. cellulose and hemicellulose into fermentable sugars. If done enzymatically this requires a large number of different enzymes with different modes of action. The enzymes can be added externally or microorganisms growing on the biomass may provide them.

The catalyst composition consists of the catalyst, the carrier, and other additives/ingredients used to introduce the catalyst to the process. As discussed above, the catalyst may comprise at least one enzyme or microorganism which converts at least one of the compounds in the biomass to a compound or compounds of lower molecular weight, down to, and including, the basic sugar or carbohydrate used to make the compound in the biomass. The enzymes capable of doing this for the various polysaccharides such as cellulose, hemicellulose, and starch are well known in the art and would include those not invented yet.

The catalyst composition may also comprise an inorganic acid preferably selected from the group consisting of sulfuric acid, hydrochloric acid, phosphoric acid, and the like, or mixtures thereof. The inorganic acid is believed useful for processing at temperatures greater than 100° C. The process may also be run specifically without the addition of an inorganic acid.

It is typical to add the catalyst to the process with a carrier, such as water or an organic based material. For mass balance purposes, the term catalyst composition therefore includes the catalyst(s) plus the carrier(s) used to add the catalyst(s) to the process. If a pH buffer is added with the catalyst, then it is part of the catalyst composition as well.

Cellulose is hydrolysed into glucose by the carbohydrolytic cellulases. The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanascs (The Enzyme Commission number (EC number)) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves of glucose units from cellooligosaccharides.

The different sugars in hemicellulose are liberated by the hemicellulases. The hemicellulytic system is more complex than the cellulolytic system due to the heterologous nature of hemicellulose. The system involves among others endo-1,4-p-D-xylanases (EC 3.2.1.8), which hydrolyse internal bonds in the xylan chain; 1,4-p-D-xylosidases (EC 3.2.1.37), which attack xylooligosaccharides from the non-reducing end and liberate xylose; endo-1 sl-p-Dvmannanases (EC 3.2.1.78), which cleave internal bonds; 1,4-β-D-malmosidases (EC 3.2.1.25), which cleave mannooligosaccharides to mannose. The side groups are removed by a number of enzymes; α-D-galactosidases (EC 3.2.1.22), α-L-arabino-furanosidases (EC 3.2.1,55), α-D-glucuronidases (EC 3.2.1.139), cinnamoyl esterases (EC 3.1.1.-), acetyl xylan esterases (EC 3.1,1,6) and feruloyl esterases (EC 3.1,1.73).

In combination with pre-treatment and/or enzymatic hydrolysis of lignocellulosic biomasses, it has been found that the use of oxidative enzymes can have a positive effect on the overall hydrolysis as well as the viability of the microorganisms employed for e.g. subsequent fermentation.

The reason for this effect is the oxidative crosslinking of lignins and other phenolic inhibitors as caused by the oxidative enzymes. Typically laccase (EC 1.10.3.2) or peroxidase (EC 1.1 1,1.7) are employed either externally or by incorporation of a laccase gene in the applied microorganism.

Because the ligno-cellulosic biomass may contain starch, the important enzymes for use in starch hydrolysis are alpha-amylases (1,4-α-D-glucan glucanohydrolases, (EC 3.2.1.1)). These are endo-acting hydrolases which cleave 1,4-α-D-glucosidic bonds and can bypass but cannot hydrolyse 1,6-α-D-glucosidic branchpoints. However, also exo-acting glycoamylases such as beta-amylase (EC 3.2.1.2) and pullulanase (EC 3.2.1.41) can be used for starch hydrolysis. The result of starch hydrolysis is primarily glucose, maltose, maltotriose, α-dextrin and varying amounts of oligosaccharides. When the starch-based hydrolysate is used for fermentation it can be advantageous to add proteolytic enzymes. Such enzymes may prevent flocculation of the microorganism and may generate amino acids available to the microorganism. Therefore, if the biomass contains starch, then glucose, maltose, maltotriose, α-dextrin and oligosaccharides are examples of a water soluble hydrolyzed species obtainable from the hydrolysis of the starch containing biomass and the afore mentioned alpha-amylases are specific examples, as well as those mentioned in the experimental section, of catalysts for the hydrolysis of starch.

In various embodiments, the hydrolysis enzyme(s) used may be recombinant, which in addition to allowing for quantities of enzyme to be produced by known techniques, also allows for modifications of the enzyme(s) to, for example, increase a desired trait of the enzyme or modify the enzyme(s) to include additional features, such as a His-tag, which allows high affinity capture, for example, onto a support.

In various embodiments, the hydrolysis enzymes may be free in solution, or immobilized onto a support. In various embodiments, the support onto which the enzymes are immobilized may be any suitable material, which are well known in the art, such as plastic, metal, and glass, and may be in the form of any desired shape, such as a disc, bead, netting, grid, rod, etc., and may include walls of a vessel or pipe, such as a reaction vessel or container. In addition, the hydrolysis enzymes may be chemically bonded, that is, covalently attached to the support, or the hydrolysis enzymes may be associated with the support by non-covalent means, such as electrostatic interactions, charge attraction, etc. In various embodiments, the enzyme(s) may be attached to a support via a linker moiety. For example, a polyethylene glycol or peptide chain may be conjugated to the enzyme(s) at one end and associated with the support on the other end. In one embodiment, the linker may be a hetero- or homo-bifunctional crosslinking agent which allows conjugation to the enzyme and the support. Additionally, a branched linker moiety may be employed, such that the local concentration of enzymes can be increased. Further, because the length of the linker moiety can be selected, and can be at various lengths, the accessibility of the enzyme(s) to the carbohydrate material can be increased.

In one embodiment, the enzyme(s) may be immobilized by absorbing onto solid porous supports. Specifically, a fluid containing the enzyme under high pressure (such as 25 to 50 Mpa) is used to immobilize the enzyme on the porous support (such as silica). The resulting porous support contain more immobilized enzyme than would otherwise have been obtained by a process carried out at atmospheric pressures.

In various embodiments, the enzymatic process is more attractive because of environmental considerations; conversion efficiency can be enhanced by adjusting the process conditions, or by enzyme genetic modification. In addition, immobilizing cellulases onto solid supports can make the enzymatic hydrolysis more competitive because the enzyme can be recycled. For example, cellulase immobilized onto Si wafers has been shown to be re-used six times and maintain activity which is only 20% lower than that of its free counterpart. Similar behavior was observed for cellulase immobilized onto chitosan microspheres, poly(vinyl alcohol) fibers, poly(vinyl alcohol) coated $Fe_2O_3$ nanoparticles, commercial activated carbon, or polystyrene films. Cross-linked cellulase aggregates prepared by precipitation in chilled n-propanol and chemically cross-linking with glutaraldehyde has been shown to be reused three times without loss of activity.

The amount of hydrolysis enzyme(s) present are often represented in Filter Paper Units (FPU)/g dry material. 1 FPU equals the amount of enzyme necessary to hydrolyse I umol/min of glycosidic bonds on Whatmann #1 filter paper, under specified conditions well known to a person skilled in the art. However, enzymatic activity could in principle be supplied in any conceivable form including through the addition of microorganisms giving rise to the desired enzymatic activity. In one embodiment, the amount of enzymes added corresponds to 0.001-15 FPU/g dry matter, preferably 0.01-10 FPU/g dry matter, more preferably 0.1-8 FPU/g dry matter, more preferably 1-7 FPU/g dry matter and most preferably less than 6 FPU/g, although depending on the starting material, other amounts of enzymes, and ratios of the various enzymes, are contemplated.

Treatment time for enzymatic hydrolysis are typically in the range of 0-72 hours, preferably 1-60 hours, more preferably 2-48 hours and more preferably 3-24 hours such as 4-24 hours, such as 6-24 hours, such as 8-24 hours, such as 10-24, such as 12-24 hours, such as 18-24 hours or 22 hours.

Temperature for enzymatic hydrolysis may be adjusted with reference to the optimum temperatures of the applied enzymatic activities, and are typically in the range of about 0-105° C. In various embodiments, the temperature range may be selected from one of the following ranges: 10-100° C., 15-90° C., 20-80° C., 25-70° C., 30-70° C., 40-45° C., or room temperature. pH of the reaction mixture call be adjusted with reference to the optimum pH of the applied enzymatic activities, and include pH ranges of: 3-12, 5-10, 6-9, 7-8, and 4-11. The enzymatic treatment can be conducted as a batch, fed batch or a continuous process.

These above embodiments are not designed to limit the specification or claims, as there are many configurations available to one of ordinary skill, which include a series of continuous vessels, or semi batch reactors or in combination with or without plug flow reactors.

The hydrolysis of the thermally treated ligno-cellulosic biomass produces an hydrolyzed mixture comprising soluble oligomeric and monomeric sugars, insoluble glucans and xylans which have not been hydrolyzed and lignin.

In a preferred embodiment, the hydrolyzed mixture is subjected to fermentation in the presence of a microorganism, under suitable conditions to convert at least a portion of the soluble sugars to an end product, preferably ethanol. Yeasts are preferred microorganisms and fermentation of ligno-cellulosic derived soluble sugars is well known to any person skilled in the art. Fermentation may be conducted while enzymatic hydrolysis still occurs, according for instance to the very well-known in the art Simultaneous Saccharification and Fermentation (SSF) process.

Solid Residue Composition

A solid residue is present in the hydrolyzed mixture and the fermented mixture.

Inventors discovered that the solid residue, either after hydrolysis and after fermentation, is a novel composition with unique properties.

The solid residue may be separated from the hydrolyzed mixture or the fermented mixture and separation may be done by means of any mechanical, physical and chemical techniques and a combination thereof. For instance, separation may be done by means of a press, a centrifuge, by decanting or by thermal evaporation or distillation.

A washing step of the solid composition may be done to remove at least in part soluble sugars and/or enzymes or other components of the hydrolyzed or fermented mixture which are adsorbed on the solid.

The solid residue composition is a novel composition comprising insoluble xylans, glucans and lignin.

As in the case of the thermally treated ligno-cellulosic biomass, either before and after fiber shives reduction, and depending on the feedstock selection and the specific thermal pretreatment, the percent lignin content of the thermally pretreated ligno-cellulosic biomass may be greater than 20%, preferably greater than 25%, more preferably greater than 30%, even more preferably greater than 40%, and most preferably greater than 50%.

It is noted that during hydrolysis and/or fermentation there is not aggregation of fibres and fiber shives to form new fiber shives, thereby the content of fiber shives in the solid composition is not greater than the content of fiber shives in the solid thermally treated ligno-cellulosic biomass after fiber shives reduction. In a preferred embodiment, the content of fiber shives in the solid portion of the hydrolyzed mixture is less than the content of fiber shives in the solid thermally treated ligno-cellulosic biomass after fiber shives reduction.

As preferably the enzymatic cocktail does not modify significantly the polymerization degree of the lignin of the thermally treated ligno-cellulosic biomass after fiber shives reduction, the lignin of the solid residue composition will be further characterized by properties similar to the lignin of the thermally treated ligno-cellulosic biomass after fiber shives reduction.

Thereby, the lignin of the solid residue may be characterized by having a percent amount of β-O-4 bonds, expressed as number of β-O-4 bonds per 100 phenyl propane units, which may be greater than a value selected from the group consisting of 10%, 20%, 25%, 30%, 35%, 40%, 45% and 50%.

The molar concentration of β-O-4 bonds may be expressed also as amount of mmol of β-O-4 bonds per gram of solid residue on a dry basis, as determined by means of 31P NMR, which may be greater than a value selected from the group consisting of 0.3 mmol, 0.5 mmol, 0.8 mmol, 1.0 mmol, 1.2 mmol, and 1.5 mmol per gram of the solid composition on a dry basis.

The lignin of solid residue may be further characterized by having a aliphatic hydroxyl content which is greater than 1 mmol, 1.5 mmol, 2 mmol, 2.5 mmol, 3 mmol, 3.5 mmol, and 4 mmol per gram of solid composition on a dry basis.

The lignin of the solid residue reduction may be further characterized by the ratio S/G of syringyl units to guaiacyl units as determined by 31P NMR. The ratio S/G may be less than a value selected from the group consisting of 2.5, 2, 1.8, 1.5, 1.2, 1.0, and 0.8.

The solid residue composition will comprise less glucans than the thermally treated ligno-cellulosic biomass, either before and after fiber shives reduction, thereby it may be further characterized by having a specific ratio of the amount of glucans to the amount of lignin which may be less than a value selected from the group consisting of 1.2, 1.0, 0.8, 0.5, and 0.3. Namely, considering for example the sample S2-ASR, it may be characterized by a glucans to lignin ratio of 2.06 (as reported in Table 2 in experimental section). Performing enzymatic hydrolysis at a hydrolysis yield of 30%, thereby leaving a certain amount of glucans in the solid residue composition, the solid composition of obtained after hydrolysis of S2-ASR will be characterized by a ratio glucans to lignin ratio of 1.477, which decreases to 1.05 in the case of hydrolysis yield of 50% and to 0.633 in the case of hydrolysis yield of 70%. The hydrolysis yield corresponds to a combination of hydrolysis parameters, such as hydrolysis time, activity and amount of enzymatic cocktail, which a skilled artisan may easily define.

The solid residue composition is further characterized by having a low glucans accessibility.

Glucans accessibility of the solid composition is defined as the percent amount of insoluble glucans of the solid composition which are enzymatically hydrolyzed to soluble compounds with respect to the amount of insoluble glucans in the solid composition, when hydrolysis is conducted in excess of enzymes and for a long hydrolysis time, according to the protocol defined in the experimental section.

In the case that the enzymatic hydrolysis of the thermally treated biomass after fiber shives reduction has been conducted in hydrolysis conditions so as to remove all the accessible glucans, the solid composition will not have accessible glucans—even if it may still have glucans which are not accessible to enzymes—and glucans accessibility is 0.

In a preferred embodiment, enzymatic hydrolysis is conducted in conditions to remove the most portion, but not all, of the glucans accessible to enzymes. Thereby, the glucans accessibility of the solid composition may be greater than zero, and preferably less than the thermally treated ligno-cellulosic biomass after shives reduction.

The glucans accessibility of the solid composition may be less than a value selected from the group consisting of 80%, 75%, 70%, 60%, 50%, 40%, and 30%.

This can be explained by a simple model: for example, consider a thermally treated ligno-cellulosic biomass after shives reduction having a glucans accessibility of 90% and subjected to a hydrolysis process with a glucan yield of 80%.

The solid composition will have 20% of the starting glucans, but only 10% are still accessible, thereby the calculated glucans accessibility of the solid composition is 50%.

As it is desirable to separate the most liquid portion from the solid composition, the dry matter of the solid composition is preferably greater than 20%, more preferably greater than 25%, even more preferably greater than 30%, even yet more preferably greater than 35%, and most preferably greater and 40%.

Even if it is desirable to remove the most part of liquid and soluble components, some of them may be still contained in the solid composition, Thereby, the solid composition may further comprise a portion of soluble enzymes which are adsorbed on the composition, and a small portion of soluble sugars—xylose, glucose and related oligomers—which have not been completely separated from the insoluble components.

The solid residue composition may be further used as a feedstock for producing different products, which may be obtained from the insoluble sugars—glucans and xylans—and or from the lignin of the solid composition.

Use and Transportation of the Low Viscosity Slurry

The low viscosity slurry of the thermally treated ligno-cellulosic biomass may be created in a slurry creation unit and then transported as a slurry stream to a remote conversion unit, where the slurry stream are converted to one or more products. Namely, the inventors have found that the slurry streams have a viscosity which is sufficient low for permitting the transportation of the slurry streams from the slurry creation unit to remote conversion unit or units by means of pipelines.

In one embodiment, the thermally treated ligno-cellulosic biomass after fiber shives reduction is dispersed into a carrier liquid to create a slurry stream or streams. In another embodiment, the thermally treated ligno-cellulosic biomass is dispersed into a carrier liquid to create a slurry stream or streams and then subjected to fiber shives reduction. The amount of carrier liquid in the slurry stream or streams may therefore be varied before, during or after fiber shives reduction, on the basis of the requirements of the specific mean or means used for fiber shives reduction.

The low viscosity slurry stream or streams may be transported in the pipeline distribution system at a high dry matter content by weight of the amount of the thermally treated ligno-cellulosic biomass after fiber shives reduction in the slurry. The dry matter content of the low viscosity slurry stream or streams by weight is preferably greater than 5%, 7%, 10%, 12%, 15%, 18%, 20%, 25%, 30%, 35%, 40% and less than 60% of the total weight of the low viscosity slurry stream or streams.

The conversion of the thermally treated ligno-cellulosic biomass after fiber shives reduction to the low viscosity slurry stream or streams occur in a slurry conversion unit, which physically comprises means for preparing the slurry. These means may comprise one or more vessels for adding and mixing the thermally treated ligno-cellulosic after fiber shives reduction to the liquid carrier. The addition of the thermally treated ligno-cellulosic after fiber shives reduction to the liquid carrier may occur in a continuous or semi-continuous way. The slurry may be formed also by adding the carrier liquid to the thermally treated ligno-cellulosic biomass after fiber shives reduction, preferably in a continuous or semi-continuous way. Again, the carrier liquid may be added to the thermally treated ligno-cellulosic before or during the fiber shives reduction within the scope of the present disclosure. In a preferred embodiment, the slurry conversion unit further comprises means for thermally treating and mechanically the ligno-cellulosic biomass reducing the fiber shives.

Once the ligno-cellulosic biomass feedstock is converted to one or more low viscosity slurry streams in the slurry creation unit, the slurry stream or streams are transported from the slurry creation unit to one or more conversion units by means of a pipeline distribution system. The pipeline distribution system connects the slurry creation unit and at least one conversion unit, which can be separated by a long or very long distance. The distance is limited by the energy and cost needed for transporting the slurry from the slurry creation unit to the conversion unit. Preferably, the distance between the slurry creation unit and the conversion unit is less than 200 Km, more preferably less than 50 Km, even more preferably less than 30 Km, most preferred less than 20 Km, being less than 10 Km the even most preferred distance. Even if the transportation may occur at very short distance, in the limit case being the slurry creation unit and the conversion unit located in a unique plant, it is preferable that the distance between the slurry creation unit and the conversion unit is greater than 500 m, more preferably greater than 1 km. In another embodiment, more than one low viscosity slurries are generated from the thermally treated ligno-cellulosic biomass in different slurry creation units, and transported between slurry creation units and conversion units and/or between different slurry creation units and/or between different conversion units by means of pipeline distribution systems. Thereby, the ligno-cellulosic biomass feedstock may be converted to different products, and the conversion to different products may occur in different remote conversion units. The conversion may occur sequentially, thereby the ligno-cellulosic biomass feedstock is first converted to a low viscosity slurry stream in a slurry creation unit and the slurry is transported to a first conversion unit; the slurry may be converted in the first conversion unit to a first product and the conversion to the first product further produces a residue stream, derived from the ligno-cellulosic biomass feedstock, which may be transported to a second conversion unit, where it may be converted to a second product. For instance, the slurry of the ligno-cellulosic biomass feedstock may be partly converted to ethanol in a first conversion unit, the conversion further producing a residue stream, which is a by-product of the first conversion, and the residue stream may be transported to a second conversion unit by means of a pipeline transmission system, where it may be converted to a second product, such as phenols and/or aromatic compounds. The process is not limited to the conversion of the ligno-cellulosic biomass feedstock to one or two products, and it may be extended to more than two products, converted in the same conversion unit or in more conversion units, simultaneously and/or sequentially, according to the described procedure. This feature is relevant for increasing the size on the distributed conversion system, for instance by collecting the feedstock in each slurry conversion unit from local sources of feedstock, thereby limiting the need of road transportation.

Preferably, the ligno-cellulosic biomass feedstock is collected in the slurry creation unit or close to the slurry creation unit. The ligno-cellulosic biomass feedstock may be grown in the area around the slurry creation unit so to minimize the road transportation distance and cost. Depending on the harvesting seasonality and plant operational planning, the ligno-cellulosic biomass feedstock may be stored for a certain time in the slurry creation unit or close to the slurry creation unit. The ligno-cellulosic biomass feedstock is converted to a low viscosity slurry stream and the slurry is transported to a remote conversion unit by means of a pipeline distribution unit. Preferably, the mean velocity of the slurry in the pipeline distribution unit is less than 5 m/s, more preferably less 3 m/s, even more preferably less than 2 m/s, being less than 1 m/s the most preferred. The pipeline distribution unit comprises a pipeline, a pipeline input and a pipeline output, connected to the slurry creation unit or to the conversion unit, and optionally one or more pump stations, which may be needed for increasing the flow of the low viscosity slurry stream over a long distance. The pump station may comprise centrifugal pumps, gear pumps, positive displacement pumps, depending on the viscosity of the slurry to be pumped. The distance between two pump stations may vary from 1 m to 1 Km, depending on the viscosity of the slurry streams and the velocity/flow of the low viscosity slurry streams. Means for the introduction/extraction of the low viscosity slurry stream in the pipeline may be comprised in the pipeline distribution unit or in the pre-treatment/conversion units. A pipeline distribution unit may be used for transporting a low viscosity slurry stream in both directions, that is the flow of the low viscosity slurry stream may be reversed. It is noted that a pipeline distribution unit may also be used for transporting other low viscosity slurry or liquid streams, not derived from ligno-cellulosic biomass feedstock, from one slurry creation unit to a conversion unit, or vice versa, or between two slurry creation units, or between two conversion units.

According to one embodiment, the ligno-cellulosic biomass feedstock may be converted to many low viscosity slurry streams in the slurry creation unit. The low viscosity slurry streams may be mixed together in the slurry creation unit and transported to the conversion unit in a unique pipeline distribution unit. In another embodiment, the low viscosity slurry streams are transported in separated pipeline distribution units to the conversion unit. The pipeline distribution units may be grouped together to form a pipeline distribution system, optionally sharing pumping stations. A pipeline distribution system may comprise one or more pipeline distribution units.

A conversion unit may be connected to more than one slurry creation unit. For instance, the ligno-cellulosic biomass feedstock may be converted in two low viscosity slurry streams. The two low viscosity slurry streams are transported to the conversion units by means of the two separated pipeline distribution systems.

A slurry creation unit may be connected to more conversion units by means of many pipeline distribution systems, each one connecting the slurry creation unit to one conversion unit. This is particularly useful in the case that the low viscosity slurry streams have different compositions and are therefore converted to different products. For instance, a first low viscosity slurry stream may comprise a relevant portion of the C5 complex sugars of the ligno-cellulosic biomass feedstock, and it may be transported to a first conversion unit, where it is converted to ethylene glycol, and a second low viscosity biomass slurry stream may comprise a relevant portion of the C6 complex sugars of the ligno-cellulosic biomass feedstock and it may be transported to a second conversion unit, where it is converted to ethanol.

A slurry creation unit may be connected to one or more other slurry creation units by means of one or more pipeline distribution systems. For instance, a first slurry creation unit may be connected with a second slurry creation unit and the second slurry creation unit may be connected then to the conversion unit. So, in this case the low viscosity slurry stream is transported from the first slurry creation unit to the conversion unit through a second slurry creation unit, by means of two pipeline distribution systems, connecting the second conversion unit to the first slurry creation unit and to the conversion unit respectively.

A conversion unit may be connected to one or more other conversion units by means of one or more pipeline distribution systems. For instance, a first conversion unit may be connected to a second conversion unit by means of the pipeline distribution system. The first conversion unit is also connected to a slurry creation unit by means of another pipeline distribution unit. The low viscosity slurry stream, obtained from the ligno-cellulosic biomass feedstock in the slurry creation unit, may be converted to a first product in the first conversion unit, the conversion further producing a residue stream, which is a low viscosity slurry stream, and the residue slurry stream may be transported to the second conversion unit, where it may be further processed for producing a second product. In one embodiment, the complex sugars are converted to ethanol in the first conversion unit, and the conversion produces residue composition comprising all the lignin, or almost all, of the ligno-cellulosic biomass feedstock. The lignin may be modified by the conversion process. The residue composition may be or may be converted to a low viscosity slurry stream and transported to the second conversion unit by means of the pipeline distribution systems, where it may be converted to further products, such as phenols or aromatic compounds. The residue of the conversion in the second conversion unit may be transported to a third conversion unit, where they can be converted further. It is noted that the conversion unit comprises also the case of waste water treatment facility, where the residue stream is converted typically by means biological processes, such as anaerobic and aerobic digestion process, to streams with low carbon content and having a low biological activity. In this case, the conversion process further produces methane-rich or hydrogen-rich gas which are useful product.

The slurry creation unit means to convert the ligno-cellulosic biomass feedstock to one or more low viscosity biomass slurry streams; means for injecting the one or more low viscosity biomass slurry stream in at least one pipeline distribution system. The conversion to one or more low viscosity biomass slurry streams is realized by means of equipments for thermally pre-treating the ligno-cellulosic biomass feedstock to produce a thermally pretreated ligno-cellulosic biomass, said means preferably comprising an equipment for steam exploding the ligno-cellulosic biomass feedstock; means for reducing the fiber shives of the thermally pretreated ligno-cellulosic biomass, said means preferably comprising an extruder, more preferably a twin screw extruder; means for forming one or more low viscosity biomass slurry streams by mixing the sheared ligno-cellulosic biomass and a liquid. Preferably the conversion of the ligno-cellulosic biomass feedstock to one or more low viscosity biomass slurry streams occurs in a continuous or semi-continuous way. The slurry creation unit may further comprise devices and equipment for treating a portion of the thermally pretreated stream before or after fiber shives reduction by means of an hydrolysis catalyst. The slurry creation unit further comprises means for connecting the devices and equipments of the slurry creation unit and transporting the ligno-cellulosic biomass feedstock between the devices and equipments of the slurry creation unit.

The conversion unit comprises means for converting one or more low viscosity biomass slurry streams. It should be noted that each low viscosity biomass slurry stream may be converted to one or more products.

The low viscosity biomass slurry stream may be converted to any product known in the art which is obtainable from the conversion of the ligno-cellulosic biomass feedstock.

In one embodiment, the ligno-cellulosic biomass feedstock is subjected to the thermal treatment and to the fiber shives reduction, then a low viscosity slurry stream is formed by mixing the thermally ligno-cellulosic biomass after fiber shives reduction with a carrier liquid. At least a portion of the liquid carrier may be added also before and/or during the fiber shives reduction step. The low viscosity slurry stream is then injected into the pipeline distribution system. Optionally additives may be added during the fiber shives reduction step or the slurry formation, for improving the mixing of the carrier liquid and the thermally treated ligno-cellulosic biomass. These additives may also include anti-freeze liquids, such as ethylene glycol, which can be useful for reducing the viscosity of the slurry stream at low temperature, which may be reached during winter season.

another embodiment, the thermal treatment produces two thermally treated ligno-cellulosic biomass streams, which can be processes to create two separated low viscosity slurry streams, which are the injected into two separated pipeline distribution units or systems. the second thermally treated ligno-cellulosic biomass stream is a low viscosity slurry stream which may be injected into the pipeline distribution unit or system without any further process. Optionally, a portion or at least a portion of the second low viscosity slurry stream may be added as an additional liquid carrier in the slurry formation step. Optionally, the second low viscosity slurry stream may be the unique carrier liquid used in the formation of the first low viscosity slurry stream. The second thermally treated ligno-cellulosic biomass may be optionally converted to the second low viscosity slurry stream.

In a further embodiment, a portion of the thermally treated ligno-cellulosic biomass and or a portion of the thermally treated ligno-cellulosic biomass after fiber shives reduction are removed from the respective streams subjected to a viscosity reduction process, preferably in the presence of a hydrolysis catalyst. The preferred hydrolysis comprises an enzyme or enzyme cocktail, and the process is conducted according to well-known process of viscosity reduction techniques. The hydrolysis catalyst may comprise also mineral or organic acids, or a base. Once the viscosity has been reduced to produce an additional low viscosity stream, the additional low viscosity stream is added in the slurry creation step as an additional carrier liquid. Optionally, the additional low viscosity stream is the carrier liquid used in the slurry creation step.

In a preferred embodiment, the ligno-cellulosic biomass feedstock is subjected to a thermal treatment comprising steam explosion to create the thermally treated ligno-cellulosic biomass, then it is converted to a low viscosity slurry stream and injected into a pipeline distribution unit or system.

In an even more preferred embodiment, the ligno-cellulosic biomass feedstock is subjected to a soaking step to produce a soaked ligno-cellulosic biomass, thereby a liquid stream is separated from the ligno-cellulosic biomass. The liquid stream may comprise a portion of the C5 sugars of the ligno-cellulosic biomass, and is a low viscosity stream, which may be added as a carrier liquid in the slurry creation step. Optionally, the liquid stream is the carrier liquid used in the slurry creation step. The ligno-cellulosic biomass feedstock may be converted to one low viscosity slurry stream. In another embodiment, at least a portion of the liquid stream obtained from the soaking step is injected to a separated pipeline distribution unit or system as a separated low viscosity stream.

Any process known in the art and still to be invented may be used in the conversion unit for converting the low viscosity biomass slurry streams. Conversion processes may include biological, physical and chemical processes, or a combination thereof. The conversion may be a direct conversion to the product, such as a one-step conversion, or a may include the conversion to intermediate compound which are further converted to the final product. Eventually the low viscosity slurry stream may be subjected to a step of separation a portion of the liquid of the low viscosity slurry stream for increasing the dry matter content by weight. Preferably the portion of the liquid which is separated does not contain, or contains a very small amount, of the pretreated ligno-cellulosic biomass.

In one embodiment, the product is obtained from the conversion of the complex sugars in the low viscosity biomass slurry stream, thereby meaning that is obtained from the conversion of the cellulose and/or the hemicellulose of the ligno-cellulosic biomass feedstock. A list of products that may be obtained from the conversion of the complex sugars is contained in "Top Value Added Chemicals from Biomass, Volume I—Results of Screening for Potential Candidates from Sugars and Synthesis Gas", August 2004, Produced by Staff at the Pacific Northwest National Laboratory (PNNL) and the National Renewable Energy Laboratory (NREL), available electronically at http://www.osti.gov/bridge. As an example, the product may be ethanol, and the conversion process may comprise the hydrolysis of the complex sugars, or a fraction of the complex sugars, in the biomass slurry stream to monomeric sugars and the fermentation of the simple sugars to ethanol. The hydrolysis may comprise the use of a hydrolysis catalyst, such as an enzyme or enzyme cocktail, or a mineral acid. The fermentation may comprise the use of a yeast. Enzymatic hydrolysis and fermentation may be conducted simultaneously, in a Simultaneous Saccharification and Fermentation process very well known in the art. As another example, the product may be ethylene glycol, which may be obtained by the conversion of the C5-based sugars of the ligno-cellulosic biomass feedstock. The conversion to ethylene glycol may occur in the presence of a inorganic catalyst by means of well-known techniques of catalytic conversion.

The product may be a biological system, such as a microorganism which is fed with the low viscosity biomass slurry stream, or with a feed derived from the low viscosity biomass slurry stream, such as a sugar stream. The product may also be produced by a microorganism which is fed with the low viscosity biomass slurry stream, or with a feed derived from the low viscosity biomass slurry stream, such as a sugar stream.

In one embodiment, the product is obtained from the conversion of the lignin in the low viscosity biomass slurry stream. A list of products that may be obtained from the conversion of the lignin in the low viscosity biomass slurry stream is contained in "Top Value-Added Chemicals from Biomass Volume II—Results of Screening for Potential Candidates from Biorefinery Lignin", J E Holladay, J J Bozell, J F White, D Johnson.

The product may be a phenols or an aromatic compound, produced by means of well-known techniques of catalytic conversion.

The conversion of the low viscosity slurry stream may further produce a residue composition, comprising some of the complex sugars and/or some of the lignin of the low viscosity biomass slurry streams, which have been eventually modified in the conversion process. The residue composition may be a low viscosity biomass slurry stream or may be converted in a low viscosity residue slurry stream, which may be transported to another conversion unit by means of a pipeline distribution system and converted to another product. As an example, the ligno-cellulosic biomass slurry stream may be converted to ethanol in a first conversion unit, the conversion further producing a residue comprising lignin, which may be transported by means of a pipeline distribution system to a second conversion unit, where it may be converted to phenols and/or aromatic compounds by means of well-known catalytic conversion process. As an alternative, the residue composition may be transported by conventional biomass transportation ways, such as road or rail.

There is a collecting area associated to each slurry creation unit, that is the area from which the ligno-cellulosic biomass feedstock is collected and transported to the slurry creation unit. Preferably, the slurry creation unit is located in the collecting area, more preferably close to the center of the collecting area. The collecting area may have an arbitrary shape. Preferably, the ligno-cellulosic biomass feedstock collected from the collecting area and converted to one or more low viscosity biomass slurry streams in the slurry creation unit corresponds to at least 50% by weight, more preferably at least 70%, even more preferably at least 90%, being the most preferably 100% of the total ligno-cellulosic biomass feedstock converted in the slurry creation unit, over a time of 1 year. Preferably, the distance between the harvesting point in the collecting area and the corresponding slurry creation unit is up to 200 Km, more preferably up to 150 Km, even more preferably up to 100 Km, even more preferably up to 80 Km, even more preferably up to 70 Km, most preferably up to 50 Km, being up to 30 Km the even most preferred distance.

In one embodiment, the distributed conversion system comprises two slurry creation units, located close to the center of the corresponding collecting areas, wherein the collecting areas are geographically separated. It should be noted that the collecting areas may in some case overlap.

In another embodiment, the distributed conversion system comprises two slurry creation units and one conversion unit, the three units being connected by a three-terminal pipeline distribution system, which may be useful for reducing pipeline installation costs. The use of pipeline distribution systems having more than two terminals, connecting many slurry creation units and/or many conversion units is in the scope of the present invention.

Based on the same motivation of reducing pipeline installation costs, in a preferred embodiment the distributed conversion system comprising two slurry creation units 1 and 2 and one conversion unit, wherein the slurry creation unit 2 is connected to the slurry creation unit 1 and to the conversion units by means of two pipeline distribution systems. In this case, the slurry creation unit 1 is connected to the conversion unit through the slurry creation unit 2. Thereby, according to the disclosed process, the low viscosity biomass slurry stream produced in the slurry creation unit 1 is transported to the slurry creation unit 2 and then from the slurry creation unit 2 to the conversion unit. Optionally, a fraction of the low viscosity biomass slurry stream produced in the slurry creation unit 1 may be converted in the slurry creation units 2.

Feedstock Selection

Because the feedstock may use naturally occurring ligno-cellulosic biomass, the stream will have relatively young carbon materials. The following, taken from ASTM D 6866-04 describes the contemporary carbon, which is that found in bio-based hydrocarbons, as opposed to hydrocarbons derived from oil wells, which was derived from biomass thousands of years ago. "[A] direct indication of the relative contribution of fossil carbon and living biospheric carbon can be as expressed as the fraction (or percentage) of contemporary carbon, symbol $f_C$. This is derived from $f_M$ through the use of the observed input function for atmospheric $^{14}C$ over recent decades, representing the combined effects of fossil dilution of the $^{14}C$ (minor) and nuclear testing enhancement (major). The relation between $f_C$ and $f_M$ is necessarily a function of time. By 1985, when the particulate sampling discussed in the cited reference [of ASTM D 6866-04, the teachings of which are incorporated by reference in their entirety] the $f_M$ ratio had decreased to ca. 1.2."

Fossil carbon is carbon that contains essentially no radiocarbon because its age is very much greater than the 5730 year half life of $^{14}C$. Modern carbon is explicitly 0.95 times the specific activity of SRM 4990b (the original oxalic acid radiocarbon standard), normalized to $\delta^{13}C=-19\%$. Functionally, the faction of modern carbon=(1/0.95) where the unit 1 is defined as the concentration of $^{14}C$ contemporaneous with 1950 [A.D.] wood (that is, pre-atmospheric nuclear testing) and 0.95 are used to correct for the post 1950 [A.D.] bomb $^{14}C$ injection into the atmosphere. As described in the analysis and interpretation section of the test method, a 100% $^{14}C$ indicates an entirely modern carbon source, such as the products derived from this process. Therefore, the percent $^{14}C$ of the product stream from the process will be at least 75%, with 85% more preferred, 95% even preferred and at least 99% even more preferred and at least 100% the most preferred. (The test method notes that the percent $^{14}C$ can be slightly greater than 100% for the reasons set forth in the method). These percentages can also be equated to the amount of contemporary carbon as well.

Therefore the amount of contemporary carbon relative to the total amount of carbon is preferred to be at least 75%, with 85% more preferred, 95% even preferred and at least 99% even more preferred and at least 100% the most preferred. Correspondingly, each carbon containing compound in the reactor, which includes a plurality of carbon containing conversion products will have an amount of contemporary carbon relative to total amount of carbon is preferred to be at least 75%, with 85% more preferred, 95% even preferred and at least 99% even more preferred and at least 100% the most preferred.

In general, a natural or naturally occurring ligno-cellulosic biomass can be one feed stock for this process. Ligno-cellulosic materials can be described as follows:

Apart from starch, the three major constituents in plant biomass are cellulose, hemicellulose and lignin, which are commonly referred to by the generic term lignocellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemicellulose.

Relevant types of naturally occurring biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus* radiate; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used to derive the composition is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indian grass, bermuda grass and switch grass. One classification of the grass family recognizes twelve subfamilies: These are 1) anomochlooideae, a small lineage of broad-leaved grasses that includes two genera (Anomochloa, Streptochaeta); 2) Pharoideae, a small lineage of grasses that includes three genera, including *Pharus* and *Leptaspis;* 3) Puelioideae a small lineage that includes the African genus *Puelia;* 4) Pooideae which includes wheat, barley, oats, brome-grass (*Bronnus*) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothcoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another naturally occurring ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:

1) conifers (Coniferae): there are some six hundred species of conifers. All species have secondary xylem, which is relatively uniform in structure throughout this group. Many conifers become tall trees: the secondary xylem of such trees is marketed as softwood.
2) angiosperms (Angiosperinae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood useful in this process is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale like leaves. They include conifer species e.g. pine, spruces, firs, and cedars. Wood hardness varies among the conifer species.

The term hardwood useful for this process is used to describe wood from trees that belong to the angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred naturally occurring ligno-cellulosic biomass may be selected from the group consisting of the grasses and woods. Another preferred naturally occurring ligno-cellulosic biomass can be selected from the group consisting of the plants belonging to the conifers, angiosperms, Poaceae and families. Another preferred naturally occurring ligno-cellulosic biomass may be that biomass having at least 10% by weight of it dry matter as cellulose, or more preferably at least 5% by weight of its dry matter as cellulose.

The carbohydrate(s) comprising the invention is selected from the group of carbohydrates based upon the glucose, xylose, and mannose monomers and mixtures thereof.

The feedstock comprising lignin can be naturally occurring ligno-cellulosic biomass that has been ground to small particles, or one which has been further processed. One process for creating the feedstock comprising lignin, comprises the following steps.

Preferable Pretreatment

It has been theorized that pretreatment of the feedstock is a solution to the challenge of processing an insoluble solid feedstock comprising lignin or polysaccharides in a pressurized environment. According to US 2011/0312051, sizing, grinding, drying, hot catalytic treatment and combinations thereof are suitable pretreatment of the feedstock to facilitate the continuous transporting of the feedstock. While not presenting any experimental evidence, US 2011/0312051 claims that mild acid hydrolysis of polysaccharides, catalytic hydrogenation of polysaccharides, or enzymatic hydrolysis of polysaccharides are all suitable to create a transportable feedstock. US 2011/0312051 also claims that hot water treatment, steam treatment, thermal treatment, chemical treatment, biological treatment, or catalytic treatment may result in lower molecular weight polysaccharides and depolymerized lignins that are more easily transported as compared to the untreated ones. While this may help transport, there is no disclosure or solution to how to pressurize the solid/liquid slurry resulting from the pretreatment. In fact, as the inventors have learned the conventional wisdom and conventional systems used for pressuring slurries failed when pre-treated ligno-cellulosic biomass feedstock is used.

In the integrated second generation industrial operations, pre-treatment is often used to ensure that the structure of the ligno-cellulosic content is rendered more accessible to the catalysts, such as enzymes, and at the same time the concentrations of harmful inhibitory by-products such as acetic acid, furfural and hydroxymethyl furfural remain substantially low. There are several strategies to achieve increased accessibility, many of which may yet be invented.

The current pre-treatment strategies imply subjecting the ligno-cellulosic biomass material to temperatures between 110-250° C. for 1-60 min e.g.:
Hot water extraction
Multistage dilute acid hydrolysis, which removes dissolved material before inhibitory substances are formed
Dilute acid hydrolyses at relatively low severity conditions
Alkaline wet oxidation
Steam explosion.

A preferred pretreatment of a naturally occurring ligno-cellulosic biomass includes a soaking of the naturally occurring ligno-cellulosic biomass feedstock and a steam explosion of at least a part of the soaked naturally occurring ligno-cellulosic biomass feedstock.

The soaking occurs in a substance such as water in either vapor form, steam, or liquid form or liquid and steam together, to produce a product. The product is a soaked biomass containing a first liquid, with the first liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours, or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. A low temperature soak prior to the high temperature soak can be used. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO_4$, $NH_3$, in order to achieve higher performance later on in the process. However, it is preferred that acid, base or halogens not be used anywhere in the process or pre-treatment. The feedstock is preferably void of added sulfur, halogens, or nitrogen. The amount of sulfur, if present, in the composition is in the range of 0 to 1% by dry weight of the total composition. Additionally, the amount of total halogens, if present, are in the range of 0 to 1% by dry weight of the total composition. By keeping halogens from the feedstock, there are no halogens in the lignin conversion products.

The product comprising the first liquid is then passed to a separation step where the first liquid is separated from the soaked biomass. The liquid will not completely separate so that at least a portion of the liquid is separated, with preferably as much liquid as possible in an economic time frame. The liquid from this separation step is known as the first liquid stream comprising the first liquid. The first liquid will be the liquid used in the soaking, generally water and the soluble species of the feedstock. These water soluble species are glucan, xylan, galactan, arabinan, glucolygomers, xyloolygomers, galactolygomers and arabinolygomers. The solid biomass is called the first solid stream as it contains most, if not all, of the solids.

The separation of the liquid can again be done by known techniques and likely some which have yet to be invented. A preferred piece of equipment is a press, as a press will generate a liquid under high pressure.

The first solid stream is then steam exploded to create a steam exploded stream, comprising solids and a second liquid. Steam explosion is a well known technique in the biomass field and any of the systems available today and in the future are believed suitable for this step. The severity of the steam explosion is known in the literature as Ro, and is a function of time and temperature and is expressed as in the Experimental Section.

EXPERIMENTAL

Preparation of Thermally Treated Ligno-Cellulosic Biomass

Wheat straw was used as the ligno-cellulosic biomass feedstock.

Wheat straw was subjected to a thermal treatment composed of a soaking step followed by a steam explosion step according to the following procedure.

Ligno-cellulosic biomass was introduced into a continuous reactor and subjected to a soaking treatment. The soaked mixture was separated into a soaked liquid and a fraction containing the solid soaked raw material by means of a press. The fraction containing the solid soaked raw material was subjected to steam explosion. Steam exploded products were separated into a steam explosion liquid and a steam exploded solid. Steam exploded solid is the exemplary thermally treated ligno-cellulosic biomass before fiber shives reduction used in the present experimental section and they are indicated by the -BSR (Before fiber Shives Reduction) extension following the sample code.

Pretreatment parameters of the ligno-cellulosic biomass are reported in Table 1.

Severity of each thermal treatment step $R_{01}$ and $R_{02}$ was calculated according the formula:

$R_{01} = \log_{10}(Q_1)$, wherein $Q_1 = t_1 \exp((T_1-100)/14.75)$ $R_{02} = \log_{10}(Q_2)$, wherein $Q_2 = t_2 \exp((T_2-100)/14.75)$, wherein time $t_1$ and $t_2$ is measured in minutes and temperature $T_1$ and $T_2$ is measured in Celsius.

The total severity factor $R_0$ was calculated according to the formula:

$R_0 = \log_{10}(Q_1+Q_2)$

TABLE 1

Process parameters used in the thermal treatment

| Sample | Soaking | | Steam explosion | | | | |
|---|---|---|---|---|---|---|---|
| | Temperature (° C.) | Time (minutes) | Temperature (° C.) | Time (minutes) | $R_{01}$ | $R_{02}$ | $R_0$ |
| S01-BSR | 155 | 65 | 180 | 2 | 3.43 | 2.66 | 3.50 |
| S02-BSR | 155 | 65 | 195 | 2 | 3.43 | 3.10 | 3.60 |
| S03-BSR | 155 | 65 | 187 | 8 | 3.43 | 3.46 | 3.75 |
| S04-BSR | 155 | 65 | 195 | 4 | 3.43 | 3.40 | 3.72 |
| S05-BSR | 155 | 65 | 202 | 8 | 3.43 | 3.91 | 4.03 |
| S06-BSR | 155 | 65 | 210 | 16 | 3.43 | 4.44 | 4.48 |
| S07-BSR | 158 | 65 | 201.5 | 4 | 3.52 | 3.59 | 3.86 |
| S08-BSR | 158 | 65 | 202.5 | 2 | 3.52 | 3.32 | 3.73 |

Fiber Shives Reduction of the Thermally Treated Ligno-Cellulosic Biomass

All the thermally treated ligno-cellulosic biomass were subjected to a fiber shives reduction step by means of a counter-rotating twin screw extruder (Welding Engineers Inc., model HTR 30 MM (HTR 30.22.22.22.13.E1), Blue Bell, Pa.), barrel length to screw diameter ratio of 54:1. The machine was fitted to a 25-hp motor, which has a provision to adjust the screw speed from 0 to 500 rpm. The parameters of the profile of the screws are reported in FIG. 1.

The thermally treated ligno-cellulosic biomass was treated at 250 rpm to reduce fiber shives. The thermally treated ligno-cellulosic biomass was inserted in the extruder at a temperature of 25° C. The thermally treated ligno-cellulosic biomass exited the extruder as a solid at about 25° C. The thermally treated ligno-cellulosic biomass was inserted manually in the extruder at an inlet rate of approximately 5 Kg/h on wet basis, at a moisture content of about 60%. Residence time was estimated be to approximately 3 minutes.

The specific energy consumption for fiber shives reducing a Kg of thermally treated ligno-cellulosic biomass was evaluated by the equation:

SEC=Absorbed power/$T$, wherein Absorbed power is measured in W, T is the material throughput, in Kg/h and SEC is measured in Wh/Kg.

The absorbed power is the electrical power absorbed by the electrical engine of the extruder. Thereby, the SEC parameter is an overestimation of the specific mechanical energy (SME), which is a parameter often reported in the prior art and is the mechanical energy applied to the thermally pretreated ligno-cellulosic biomass (see for example Wen-Hua Chen et al., Bioresource Technology 102 (2011), p. 10451).

The SEC was evaluated to be in the range of 0.1-0.2 kWh/Kg of thermally treated ligno-cellulosic biomass on wet basis. The specific energy consumption is much lower that the specific energy reported in the prior art, as for example in WO2011044292A2, wherein an energy of 1.03 kWh/kg is used.

The extruded thermally treated ligno-cellulosic biomass for reducing fiber shives is the exemplary thermally treated ligno-cellulosic biomass after fiber shives reduction used in the following examples and are indicated by the -ASR (After fiber Shives Reduction) extension following the sample code.

Composition

Composition of materials was determined according to standard analytical methods listed at the end of the experimental section to quantify soluble sugars (glucose, xylose, glucooligomers and xylooligomers), insoluble sugars (glucans and xylans), xylans degradation products (furans, such as furfural), glucans degradation products (HMF), and lignin and other compounds. The compositions of corresponding BSR and ASR materials were identical within the measurement error and only ASR compositions of exemplary samples (S01 to S06) are reported in Table 2. Results are reported in terms of weight percent of the dry matter of the samples. It is noted that the percent amount of glucans and xylans degradation products is negligible or very low, namely less than 1% in all the samples, thanks to the low severity of the thermal treatment. Acetic acid is produced as an effect of the thermal treatment on the acetyl groups in the ligno-cellulosic biomass and it is considered an enzyme inhibitory compound, but not a sugar degradation product which potentially limits the yield of the process. Also the content of acetic acid is negligible. It is noted that the percent ratio of insoluble xylans to insoluble glucans decreases with severity factor $R_{02}$, as the thermal treatment removes preferentially xylans.

TABLE 2

Composition of thermally treated biomass after fiber shives reduction.

| Composition, % wt. DB | S1-ASR | S2-ASR | S3-ASR | S4-ASR | S5-ASR | S6-ASR |
|---|---|---|---|---|---|---|
| Glucose | 0 | 0 | 0 | 0 | 0.101 | 0.088 |
| Xylose | 0 | 0.244 | 0 | 0.8 | 1.734 | 1.546 |
| Glucolygomers | 0 | 0.258 | 0 | 0.556 | 0.77 | 0.731 |
| Xylolygomers | 0 | 3.849 | 0 | 4.886 | 2.112 | 2.634 |
| Insoluble glucans | 43.658 | 46.392 | 50.271 | 47.844 | 42.705 | 44.394 |
| Insoluble xylans | 13.498 | 14.637 | 13.046 | 11.122 | 3.994 | 3.79 |
| Lignin | 20.685 | 22.498 | 23.225 | 22.61 | 21.34 | 22.723 |
| Others | 22.159 | 11.933 | 13.458 | 11.945 | 26.656 | 23.351 |
| Furfural | 0 | 0.007 | 0 | 0.024 | 0.057 | 0.08 |
| HMF | 0 | 0.024 | 0 | 0.043 | 0.119 | 0.142 |
| Acetic Acid | 0 | 0.158 | 0 | 0.17 | 0.412 | 0.521 |
| Insoluble xylans/ insoluble glucans | 0.309 | 0.316 | 0.26 | 0.232 | 0.094 | 0.085 |
| Insoluble glucans/lignin | 2.11 | 2.06 | 2.16 | 2.12 | 2.00 | 1.95 |

Glucose/Xylose Recovery and Glucans Accessibility

Glucose recovery is the percent ratio between the total amount of glucans in the thermally treated biomass before fiber shives reduction (as glucose equivalent calculated including insoluble glucans, gluco-oligomers, cellobiose and glucose present in both solid and liquid streams) and the amount of glucans (converted in glucose equivalent) present in the raw material before the thermally treatment. The complementary to 100% of the glucose recovery represent therefore the total amount of glucans degradation products as an effect of the thermal treatment.

Xylose recovery is the percent ratio between the total amount of xylans in the thermally treated biomass before fiber shives reduction (as xylose equivalent calculated including insoluble xylans, xylo-oligomers, xilobiose and xylose present in both solid and liquid streams) and the amount of xylans (converted in xylose equivalent) present in the raw material before the thermal treatment. The complementary to 100% of the xylose recovery represents therefore the total amount of xylans degradation products as an effect of the thermal treatment.

Glucans accessibility is defined as the percent amount of insoluble glucans enzymatically hydrolyzed to soluble compounds with respect to the amount of insoluble glucans in the pre-treated materials (before and after fiber shives reduction) and calculated as (1−% insoluble glucans at the end of the hydrolysis)/(% insoluble glucans at the beginning of the hydrolysis), when hydrolysis is conducted in excess of enzymes and for a long time. Glucans accessibility was determined according to the following procedure.

Pretreated material was mixed with water in a volume of 1500 ml to obtain a mixture having a 7.5% dry matter content and the mixture was inserted into an enzymatic reactor. pH was set to 5.2 and temperature was set to 50° C. An enzyme cocktail (CTec3 by Novozymes) was added, corresponding to a concentration of 26 g of cocktail solution per 100 gram of glucans contained in the mixture.

Enzymatic hydrolysis was carried out for 48 hours under agitation. The content of glucans, glucose and glucooligomers in the mixture was measured at different times of the enzymatic hydrolysis.

Glucans accessibility and xylose and glucose recovery was determined for all the BSR and ASR materials.

In FIG. 2 the glucans accessibility and in FIG. 3 the xylose and glucose recovery in function of $R_{O2}$ are reported. All the plots in this experimental section are reported in function of $R_{O2}$, as this severity factor is related to the steam explosion effect. Similar considerations hold in the case that $R_O$ is considered as the independent variable in the graphs.

It is noted that glucans accessibility of BSR material increases by increasing severity factor, but a bigger amount of xylans are degraded. The fiber shives reduction treatment is effective to increase the glucans accessibility at low severity factor, without degrading xylans (or degrading a very few amount of) to degradation products. Thereby, also at low severity factor, a glucans accessibility greater than 90% is obtained. Increasing the severity factor, the effectiveness of the fiber shives reduction treatment on glucans accessibility is less pronounced.

In the case of glucans recovery, the degradation effect is less pronounced but the effects of thermal and fiber shives reduction treatment are similar to those observed for xylans recovery.

Automated Optical Analyses

The samples were analyzed by automated optical analysis, using unpolarized light for determining fibres, fines and fiber shives content, as well as length and width. ISO 16065 2:2007 protocol was used in fibres analyses.

The instrument used was a MorFi analyser from Techpap, Grenoble, France.

Briefly, 2 g of air dried sample was disintegrated in a low consistency pulper for 2000 revolutions in approximately 2 litres of tap water, thus reaching a stock concentration of about 1 g/l.

The suspension was stirred very well before withdrawing the sample to perform the measurement according to the manufacturer's instructions. Each sample was run in duplicate or in triplicate in case of higher standard deviation.

According to Morfi analysis software, the treated lignocellulosic biomass is composed by:
Fiber shives: elements having a width greater than 75 micron
Fibres: elements having a width equal to or less than 75 micron and a length greater than 200 micron
Fines: having a width equal to or less than 75 micron and a length less than 200 micron The width of the fibres, fines and fibers shives remained substantially unchanged after the fiber shives reduction treatment.

In the graphs of FIG. 4 it is reported the area-weighted distribution of fibres and fines length of BSR and ASR materials produced at low severity factor (S02-BSR and 502-ASR, FIG. 4a) and high severity factor (S05-BSR and S05-ASR, FIG. 4b) relative to all the sample. Briefly, the percent area value of each length class has been calculated as percent ratio of the sum of the area of all the fibres and fines in each length class and the sum of the area of all the fines, fibres, and fiber shives.

It is noted that S05-BSR has a greater percent area of fines and a lower percent area of long fibres with respect to S02-BSR, as expected considering the higher severity of S05-BSR thermal treatment. This corresponds to a higher glucans accessibility of S05-BSR (about 94%) with respect to S02-BSR (84%).

The fiber shive reduction treatment reduces the percent area of long fibres (or equivalently the number of long fibres) and increases the population of fines and short fibres in both the samples, but:

the reduction of the percent area of long fibres in S05-ASR, with respect to S05-BSR, is similar to the corresponding reduction in S02-ASR;

the percent area of fines in S05-ASR is greater than in S02-ASR;

despite the fact that S05-ASR contains more fines/short fibres than S05-BSR (in other words, it is more refined), the accessibility is unchanged within the experimental error (93% and 94%);

despite the fact that S05-ASR contains more fines/short fibres than S02-ASR, the corresponding accessibility are very close (93% and 92% respectively).

In the graph of FIG. 5 it is reported the area-weighted distribution of fiber shives of S02-BSR (FIG. 5a) and S05-BSR (FIG. 5b) and related ASR materials. The percent area value of each length class has been calculated as percent ratio of the sum of the area of all the fiber shives in each length class to the sum of the areas of all the fines, fibres, and fiber shives.

It is highlighted that:

S05-BSR has a lower percent area of shives than S02-BSR, in particular shives longer than about 737 μm, evidencing that that steam explosion is effective in reducing big shives;

the percent area of shives is strongly reduced by the mechanical treatment in S02-BSR, due to the large starting shives population.

the accessibility of S02-BSR is strongly enhanced by the reduction in long shives population;

The accessibility of S05-BSR is not affected by the fiber shives reduction treatment because the limited percent area of long shives.

In the graph of FIG. 6 it is reported the percent area of all the shives having a length greater than 737 μm in function of the second severity cooking $R_{o2}$ of exemplary samples before and after fiber shives reduction. S06-BSR was produced at the maximum severity factor of $R_{o2}$ of 4.44 sufficient to remove substantially all shives. The percent area of all the shives having a length greater than 737 μm has been calculated as the percent ratio of the sum of the areas of all the shives and the sum of the areas of all the fines, fibres, and fiber shives.

These results highlight the fact that the increase in glucans accessibility is not strictly related to fibre size reduction, that is, once the fibres are accessible to the enzyme, any further decrease in fibre length is not effective on enzymatic accessibility of the fibre, thereby energy is spent without obtaining any beneficial effect on accessibility.

Instead, experiments show that it is the reduction of the amount of fiber shives to be effective on the enzymatic accessibility, depending clearly from the starting population of fiber shives. If the thermal treatment is performed at a severity high enough to produce a thermally treated material having a low amount of fiber shives, more specifically of long fiber shives, the fiber shives reduction treatment has not effect on the accessibility of the material. Unfortunately, such a high severity thermal treatment degrade a relevant amount of glucans and xylans to detrimental degradation products.

Basically, the experiments highlight that fiber shives are fiber bundles which are not accessible to the enzymes, thereby limiting the glucans accessibility, and that the fiber shives reduction treatment is useful when it convert fiber shives to fibres. As a consequence, the combination of the thermal treatment in mild conditions and the treatment to reduce the amount of fiber shives increases the glucans accessibility and xylose recovery without degrading a significant amount of sugars in the ligno-cellulosic biomass.

Torque Measurement of Slurried Samples

Torque measurement experiments were run in a cylindrical vessel whose characteristics are here reported.

D (diameter)=105 mm
H (height)=145 mm

The reactor is fitted with a stirrer tool IKA R 1375 to give the following configurations:

D (stirrer width)=70 mm
D (stirrer height)=70 mm
H (stirrer distance from the vessel bottom)=10 mm Agitation was provided by IKA Eurostar 60 control motors (power: 126 W).

With no material inserted, the no load torque at 50 rpm was 0 N cm. An amount of material corresponding to 80 gr on dry basis was inserted in the vessel and water was added to reach a dry matter of 20%.

The mixture was agitated at 50 rpm for 10 seconds. The torque value of each run was calculated as the mean of the maximum and minimum value during 5 seconds measuring time.

The measurement was replicated three times and the torque was calculated as the mean value of the three runs.

After each torque measurement at a fixed dry matter, the dry matter was reduced to 18%, 16%, 14%, 12%, 10%, 8% by subsequent addition of water. Temperature was maintained at 25° C.

In table 3 torque values of exemplary samples, collected at different dry matter, are reported. Values below the sensitivity of the measurements are reported as 0.

TABLE 3

Torque measurements of samples at different dry matter
Torque, N*cm

| DM, % | S01-BSR | S01-ASR | S02-BSR | S02-ASR | S03-BSR | S03-ASR | S04-BSR | S04-ASR | S05-BSR | S05-ASR |
|---|---|---|---|---|---|---|---|---|---|---|
| 20% | 87 | 11 | 49 | 8 | 59 | 17 | 36 | 2 | 0 | 0 |
| 18% | 54 | 7 | 40 | 6 | 45 | 10 | 20 | 1 | 0 | 0 |
| 16% | 43 | 5 | 31 | 3 | 31 | 8 | 13 | 0 | 0 | 0 |
| 14% | 25 | 5 | 19 | 2 | 17 | 5 | 8 | 0 | 0 | 0 |
| 12% | 17 | 3 | 10 | 1 | 11 | 3 | 5 | 0 | 0 | 0 |
| 10% | 9 | 1 | 6 | 0 | 8 | 1 | 1 | 0 | 0 | 0 |
| 8% | 3 | 0 | 1 | 0 | 3 | 0 | 0 | 0 | 0 | 0 |

In FIG. 7 the torque of S01 and S04 samples (BSR and corresponding ASR materials), measured at different dry matter, are plotted as an example.

In FIG. 8 the torque measured at 18% dry matter as a function of the severity factor is reported.

It is noted that at fixed dry matter the torque values decreases by increasing the thermal treatment severity factor and that samples thermally treated at the highest severity factor present a torque value which is very small—or zero—even at the high dry matter values. Torque values are dependent from the experimental setup and procedure used, but they are directly related to viscosity measurements. Thereby, viscosity strongly decrease increasing the severity factor of the thermal treatment.

By applying the disclosed fiber shives reduction treatment to the thermally treated samples, the torque values at each dry matter decrease and this effect is enhanced at low severity.

Thereby, the combination of the thermal treatment in mild conditions and the treatment to reduce the amount of fibers shives of the thermally treated biomass strongly reduces the torque/viscosity of a slurry of the corresponding thermally treated biomass after fiber shives reduction. Again, this is obtained without degrading significant amount of sugars of the ligno-cellulosic biomass.

As reported in following experimental sections, the torque/viscosity values of the slurry prepared using the thermally treated ligno-cellulosic biomass after shives reduction are comparable to the torque/viscosity values of corresponding thermally treated biomass before fiber shives reduction which have been enzymatically hydrolyzed.

Saturation Humidity

Saturation humidity is the maximum amount of water that could be absorbed by the ligno-cellulosic biomass. The water added to the material after the material has reached its saturation humidity value is not entrapped into the solid material and will be present as free water outside the solid. Material properties evaluated using the saturation humidity procedure are equivalent to those given by the well-known in the art Water Retention Value (WRV) procedure. Saturation humidity procedure is easier and could be performed without dedicated equipment with respect to WRV.

Saturation humidity is correlated to torque/viscosity of the slurried ligno-cellulosic biomass, but it is related to not-slurried ligno-cellulosic biomass.

Saturation humidity was measured according to the following methodology:

An amount of 20 gr of sample on dry matter basis was inserted in a becker and water (up to 50 ml) was added in 2 ml aliquots every 1 h and hand shaken to allow the material adsorb the water. The procedure ends when water added is not absorbed into the material after the 1 h incubation and water drops are observed on the surface of the material. Measurements were performed at 25° C. The saturation humidity is calculated as the total amount of water absorbed into the material (initial moisture content plus the amount of water added), divided by the weight of the material on a dry basis.

The saturation humidity of samples prepared at different severity factor $R_{O2}$ before and after fiber shives reduction is reported in FIG. 9. One of the effects of the disclosed fiber shives reduction treatment is to reduce the saturation humidity, and this result is also correlated to the decrease of torque/viscosity observed for ASR slurries with respect to BSR slurry. It is noted that in the prior art an increase of WRV (which is equivalent to saturation humidity) is usually related to micro-fibrillation of fibres, that is a mechanical treatment used to open up the fibres that consequently adsorb more water (see I. C. Hoeger et al., Cellulose (2013) 20:807-818).

A similar concept is expressed in S. H. Lee et al., Bioresource Technology, 2010, 101, p. 9645-9649, and in S. H. Lee et al., Bioresource Technology, 2010, 101, p. 769-774, where a thermally treated biomass is subjected to a mechanical treatment by means on an extruder operated in condition to fibrillate the feedstock into submicron and/or nanoscale fibres, even if no WRV/saturation humidity measurements are presented.

Thereby, according to the prior art consideration, the fiber shives reduction treatment presently disclosed does not fibrillate the fibres.

Comparison of Torque of Slurried Thermally Treated Biomass after Fiber Shives Reduction and Thermally Treated Biomass Before Fiber Shives Reduction During Enzymatic Hydrolysis To better demonstrate the importance of forming a low viscosity slurry from the thermally treated biomass after shives reduction without any added enzymes, a further sample was prepared, at the following conditions:

| Ligno-cellulosic biomass | Soaking | | Steam explosion | | | | |
|---|---|---|---|---|---|---|---|
| | Temperature (° C.) | Time (minutes) | Temperature (° C.) | Time (minutes) | $R_{O1}$ | $R_{O2}$ | $R_O$ |
| Wheat straw | 155 | 65 | 190 | 4 | 3.43 | 3.25 | 3.65 |

Fiber shives reduction step was performed by means of the extruder according to the process previously described.

Torque measurement experiments were run in two identical anchor impeller, herein referred to reactor A and reactor B, whose characteristics are here reported.

$T$ (reactor diameter)=0.15 m–$Z$ (reactor height)=0.30 m jacket for heat exchange fluid all around the lateral surface and bottom, with a width of 4 cm;
hemi-spherical bottom;
cover with gasket and seal, with 5 openings (1 center hole for stirrer shaft; 4 side holes to add materials or for sampling, that during the tests will be closed with caps).

The two reactors are fitted with two identical anchor agitators to give the following configurations:
D ("wingspan")=0.136 m
S (blade width)=0.019 m
H (anchor height)=0.146 m
5 C (clearance, blade-wall distance)=0.007 m Agitation was provided by Heidolph RZR 2102 control motors (power: 140 W).

With no material inserted, the no load torque at 23 rpm was 23 N cm. An amount of 800 gr of BSR material having a moisture content of 60% was inserted in reactor A and soaking liquid was added at a ratio of 1:0.67. The dry matter was progressively adjusted to reach a final dry matter of 15% by addition of water at the end of the experiment.

An amount of 800 gr of ASR material having a dry matter content of 40% was inserted in reactor B and soaking liquid was added at a ratio of 1:0.67. The dry matter was progressively adjusted to reach a final dry matter of 15% by addition of water at the end of the experiment.

Temperature in both reactors was 25° C.

The two mixtures were agitated at 23 rpm for 90 minutes with no enzymes added.

Viscosity reduction was then conducted in both reactors, at a temperature of 50° C. pH was corrected to 5 by means of a KOH solution. Viscosity reduction was conducted by inserting Ctec3 enzymatic cocktail by Novozymes at a concentration of 4.5 gr of enzyme cocktail every 100 g gram of glucans contained in the BSR and ASR solid materials. Viscosity reduction was conducted for 48 hours under agitation.

Torque was recorded for all the experiment time. No load torque was subtracted by the measured torque. The torque of the mixture comprising the material before fiber shives reduction without enzymes was approximately constant at a value close to 110 N cm till the insertion of enzymes. Then torque value was found to decrease after enzyme addition as usually occurs during hydrolysis. The torque of the mixture comprising the material after fiber shives reduction was found to be very low and close to the torque value of the hydrolyzed stream even before enzymes addition.

FIG. 10 reports torque values of the two slurries during the first 21 hours of mixing time. Torque values remained approximately constant after this period and for the remaining mixing time in both reactors. Time zero corresponds to the start of agitation. Arrows indicate enzymes addition in both reactors.

Rheological and Viscosity Measurements

Different amounts of BSR and ASR of the sample having $R_{02}$=3.25 were added to water to prepare 600 ml slurry samples at different dry matter content on dry basis, ranging from 5 to 17%. The samples were agitated up to 15 minutes until reaching a visually well dispersed slurries.

Rheological measurements were performed using a RheolabQC at 25° C. Data were collected corresponding to a shear rate ranging from 0.01 to 100 s$^{-1}$ and at a slope of 6 Pt./dec. Table 4 reports the measured shear stress and viscosity values for ASR slurries having a dry matter of 5%, 7%, 9%, 11%. The viscosity is not constant and decreases with the increase of shear rate.

It was not possible to measure BSR slurries on RheolabQC at 25° C. even at a dry matter lower than 5% due to the high viscosity of the sample. This is a remarkable difference in the rheological properties of BSR and ASR slurries.

TABLE 4

Rheological parameters of ASR slurries having a dry matter content of 5%, 7%, 9%, 11%.

| Shear Rate, 1/s | Shear Stress, Pa | | | | Viscosity, Pa · s | | | |
|---|---|---|---|---|---|---|---|---|
| | Dry matter | | | | | | | |
| | 5% | 7% | 9% | 11% | 5% | 7% | 9% | 11% |
| 0.10 | 0.72 | 0.69 | 1.11 | 18.10 | 7.2 | 6.90 | 11.1 | 181 |
| 0.15 | 0.68 | 0.82 | 0.71 | 20.30 | 4.66 | 5.60 | 4.84 | 138 |
| 0.22 | 0.63 | 1.26 | 0.62 | 23.60 | 2.9 | 5.87 | 2.9 | 110 |
| 0.32 | 0.62 | 1.84 | 0.94 | 27.70 | 1.97 | 5.82 | 2.97 | 87.7 |
| 0.46 | 1.14 | 1.63 | 1.33 | 35.10 | 2.47 | 3.50 | 2.87 | 75.7 |
| 0.68 | 0.96 | 1.53 | 0.64 | 47.70 | 1.41 | 2.25 | 0.932 | 70.1 |
| 1.00 | 1.17 | 1.16 | 1.19 | 58.10 | 1.17 | 1.16 | 1.19 | 58.2 |
| 1.47 | 0.81 | 0.67 | 1.01 | 43.20 | 0.553 | 0.45 | 0.687 | 29.3 |
| 2.15 | 0.67 | 1.00 | 1.35 | 10.70 | 0.31 | 0.47 | 0.627 | 4.94 |
| 3.16 | 1.36 | 1.77 | 1.00 | 27.10 | 0.429 | 0.56 | 0.317 | 8.61 |
| 4.64 | 0.54 | 1.11 | 1.78 | 18.50 | 0.117 | 0.24 | 0.383 | 3.97 |
| 6.81 | 0.77 | 1.33 | 1.96 | 36.60 | 0.113 | 0.20 | 0.288 | 5.36 |
| 10.00 | 0.74 | 1.56 | 3.23 | 25.30 | 0.074 | 0.16 | 0.323 | 2.53 |
| 14.70 | 1.09 | 1.64 | 4.35 | 28.20 | 0.074 | 0.11 | 0.296 | 1.92 |
| 21.50 | 1.16 | 1.89 | 5.61 | 26.20 | 0.053 | 0.09 | 0.26 | 1.21 |
| 31.60 | 1.61 | 2.05 | 5.05 | 22.40 | 0.050 | 0.06 | 0.16 | 0.70 |
| 46.40 | 0.73 | 2.75 | 4.63 | 24.90 | 0.015 | 0.06 | 0.099 | 0.53 |
| 68.10 | 0.37 | 2.45 | 5.84 | 24.30 | 0.005 | 0.04 | 0.085 | 0.35 |
| 100.00 | 0.44 | 2.62 | 4.36 | 21.60 | 0.004 | 0.03 | 0.043 | 0.21 |

Figure 11:
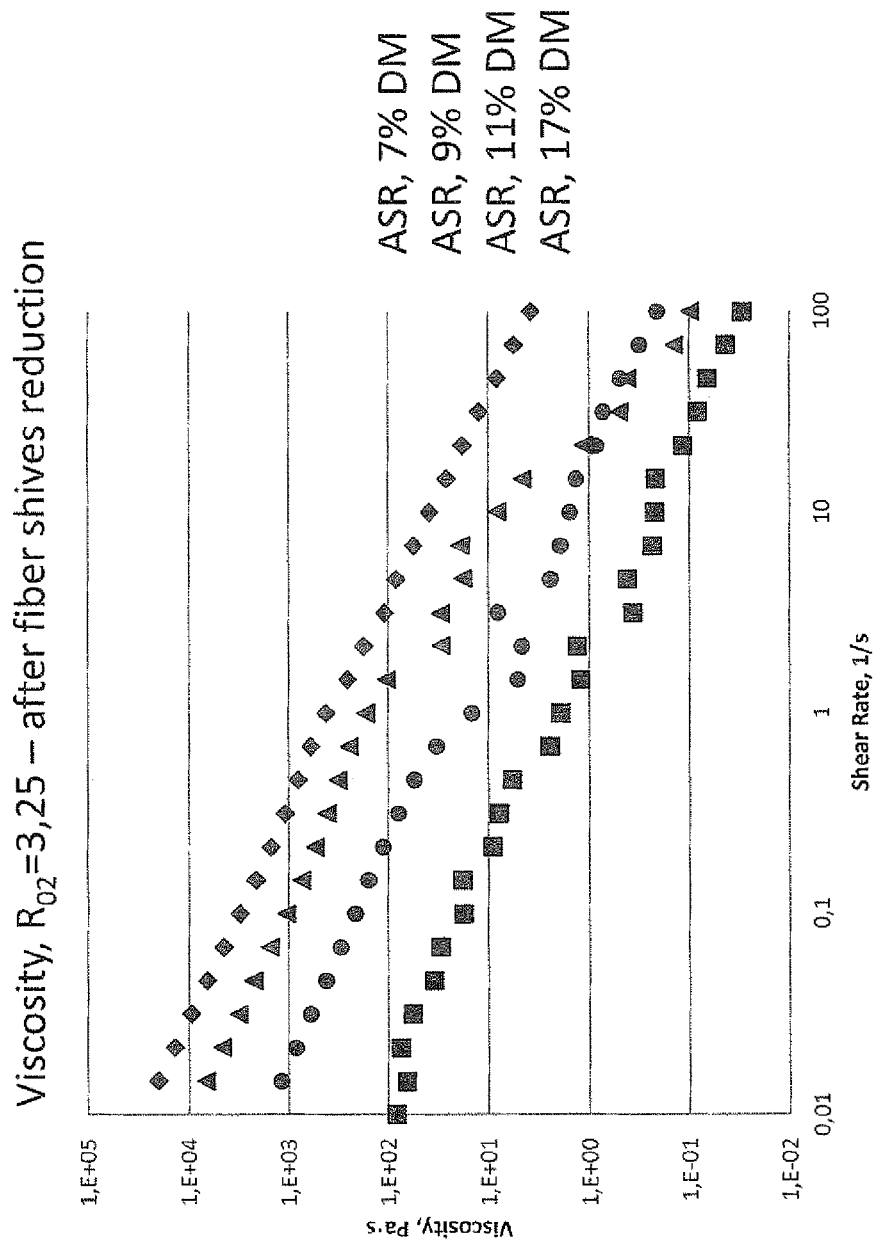
FIG. 11 plots the viscosity of slurries of the thermally treated biomass after fiber shives reduction at different amounts in water.

The viscosity of ASR slurries at 7%, 9%, 11% and 17% are reported in the graph of FIG. 11 on a bi-logarithmic scale. The vertical line in the graph indicates the shear rate value which was selected as the reference value for measuring the viscosity. In the context of the present disclosure, the described RheolabQC instrument procedure for viscosity measurement is the reference method for measuring the viscosity of a slurry.

Figure 12:
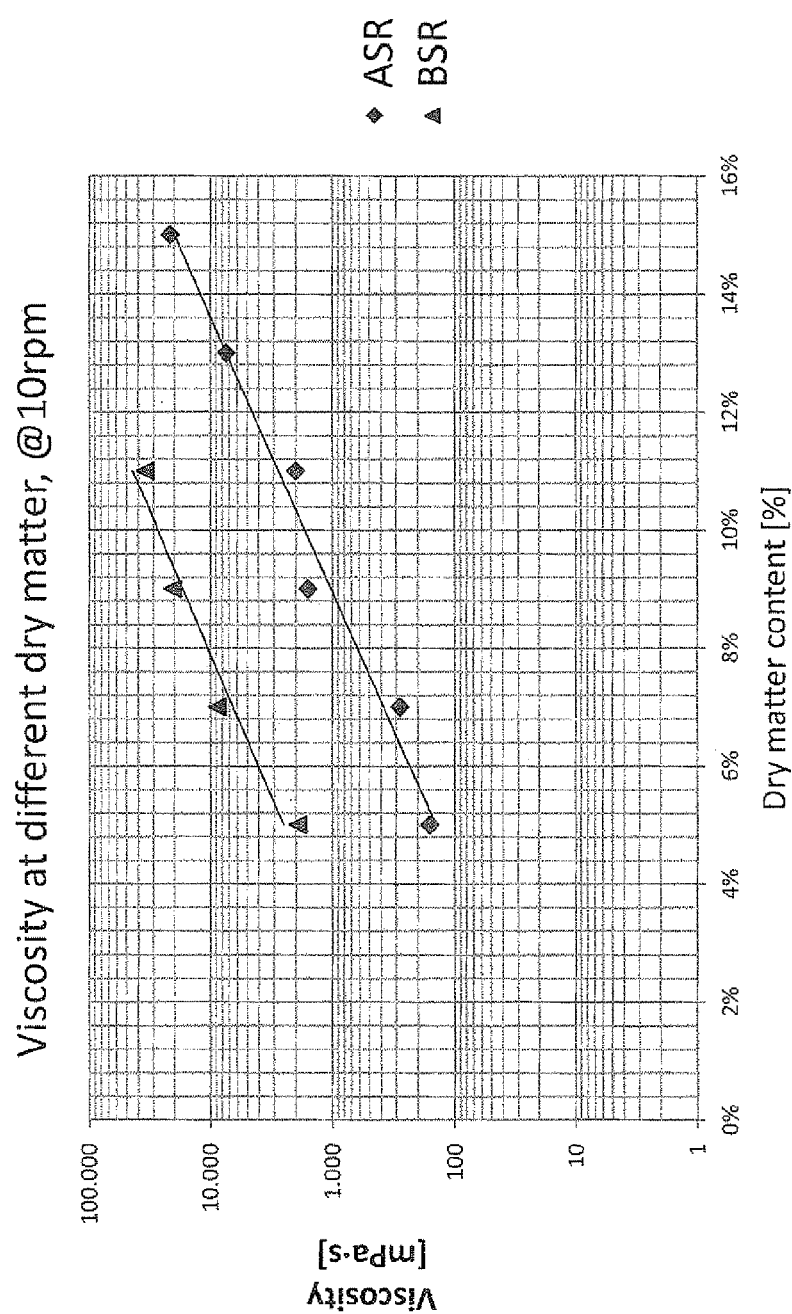
FIG. 12 plots the viscosity of slurries of thermally treated ligno-cellulosic biomass before and after fiber shives reduction at different dry matter contents of the slurry.

Viscosity measurements were performed on BSR and ASR slurry samples also using a Brookfield RVDV-I Prime viscometer following the procedures reported by the producer. All the measurements were performed at 25° C. using a disc spindle #5 on a 600 ml sample. Data were collected starting from 1 rpm and increasing the rotation speed to 2.5, 5, 10, 20, 50 and 100 rpm. In FIG. 12 viscosities of BSR and ASR slurries collected at 10 rpm as a function of dry matter are shown. The graph highlights that the viscosity of the slurry prepared using ASR is about 90% less than that prepared using BSR.

Analytical Methods

Analytical measurements were performed according to the following NREL standards Determination of Structural Carbohydrates and Lignin in Biomass Laboratory Analytical Procedure (LAP) Issue Date: Apr. 25, 2008

Technical Report NREL/TP-510-42618 Revised April 2008

Determination of Extractives in Biomass

Laboratory Analytical Procedure (LAP) Issue Date: Jul. 17, 2005

Technical Report NREL/TP-510-42619 January 2008

Preparation of Samples for Compositional Analysis

Laboratory Analytical Procedure (LAP) Issue Date: Sep. 28, 2005

Technical Report NREL/TP-510-42620 January 2008

Determination of Total Solids in Biomass and Total Dissolved Solids in Liquid Process Samples Laboratory Analytical Procedure (LAP) Issue Date: Mar. 31, 2008

Technical Report NREL/TP-510-42621 Revised March 2008

Determination of Ash in Biomass

Laboratory Analytical Procedure (LAP) Issue Date: Jul. 17, 2005

Technical Report NREL/TP-510-42622 January 2008

Determination of Sugars, By Products, and Degradation Products in Liquid Fraction Process Samples Laboratory Analytical Procedure (LAP) Issue Date: Dec. 8, 2006

Technical Report NREL/TP-510-42623 January 2008

Determination of Insoluble Solids in Pretreated Biomass Material

Laboratory Analytical Procedure (LAP) Issue Date: Mar. 21, 2008

NREL/TP-510-42627 March 2008

We claim:

1. A process for increasing the enzymatic accessibility of a steam exploded ligno-cellulosic biomass feedstock, wherein said steam exploded ligno-cellulosic biomass feedstock is free of an added base and comprised of xylans, glucans and lignin and is in physical forms of at least fibres, fines and fiber shives, wherein:
   a. the fibres each have a width of 75 μm or less, and a fibre length greater than or equal to 200 μm,
   b. the fines each have a width of 75 μm or less, and a fine length less than 200 μm,
   c. the fiber shives each have a shive width greater than 75 μm with a first portion of the fiber shives each having a shive length less than 737 µm and a second portion of the fiber shives each having a shive length greater than or equal to 737 µm, wherein the process comprises a fiber shives conversion step which is done by converting at least a portion of the fiber shives having a shive length greater than or equal to 737 µm to fines such that the percent area of fiber shives having a shive length greater than or equal to 737 µm relative to the total area of fiber shives, fibres and fines of the steam exploded ligno-cellulosic biomass after fiber shives conversion is less than the percent area of fiber shives having a shive length greater than or equal to 737 µm relative to the total area of the fiber shives, fibres and fines of the steam exploded ligno-cellulosic biomass before fiber shives conversion, wherein the percent area is measured by automated optical analysis, and wherein at least a portion of the fiber shives conversion step is done by applying a work in a form of mechanical forces to the steam exploded ligno-cellulosic biomass, and all the work done by all the forms of mechanical forces on the steam exploded ligno-cellulosic biomass is less than 500 WH/Kg per kg of the steam exploded ligno-cellulosic biomass on a dry basis.

2. The process of claim 1, wherein the mechanical forces applied to the steam exploded ligno-cellulosic biomass is not derived from free-fall or gravity mixing.

3. The process of claim 1, wherein the mechanical forces are applied using a machine selected from the group consisting of single screw extruders, twin screw extruders, and banburies.

4. The process of claim 1, wherein the steam exploded ligno-cellulosic biomass before fiber shives conversion is characterized by having a viscosity of a slurry of the steam exploded ligno-cellulosic biomass before fiber shives conversion in water which is greater than the viscosity of a slurry of the steam exploded ligno-cellulosic biomass after fiber shives conversion in water, wherein the viscosities are measured at 25° C., at a shear rate of 10 $s^{-1}$ and at a dry matter content of 7% by weight of each slurry.

5. The process of claim 1, wherein the steam exploded ligno-cellulosic biomass after fiber shives conversion is characterized by having a viscosity of a slurry of the steam exploded ligno-cellulosic biomass after fiber shives conversion in water less than 10 Pa s, wherein the viscosity is measured at 25° C., at a shear rate of 10 s' and at a dry matter content of 7% by weight of the slurry of the steam exploded ligno-cellulosic biomass after fiber shives conversion in the water.

6. The process of claim 1, wherein the percent area of the fiber shives having a shive length greater than or equal to 737 µm relative to the total area of fiber shives, fibres and fines of the steam exploded ligno-cellulosic biomass before fiber shives conversion is greater than 4%.

7. The process of claim 1, wherein the percent area of the fiber shives having a shive length greater than or equal to 737 µm relative to the total area of fiber shives, fibres and fines of the steam exploded ligno-cellulosic biomass after fiber shives conversion is less than a value 1%.

8. The process of claim 1, wherein the steam exploded ligno-cellulosic biomass has been steam exploded as part of a thermal treatment and the thermal treatment has a total severity factor.

9. The process of claim 8, wherein the total severity factor of the thermal treatment used to create the steam exploded ligno-cellulosic biomass is less than 4.0.

10. The process of claim 1, wherein the steam exploded ligno-cellulosic biomass after fiber shives conversion has a first saturation humidity, and the steam exploded ligno-cellulosic biomass before fiber shives conversion has a second saturation humidity, and the first saturation humidity is less than the second saturation humidity.

11. The process of claim 1, wherein the steam exploded ligno-cellulosic biomass before fiber shives conversion has a xylose recovery greater than 70%.

12. The process of claim 1, wherein the steam exploded ligno-cellulosic biomass before fiber shives conversion has a glucose recovery greater than 80%.

13. The process of claim 1, wherein the glucan accessibility of the steam exploded ligno-cellulosic biomass after fiber shives conversion is greater than 80%.

14. The process of claim 1, wherein the glucans accessibility of the steam exploded ligno-cellulosic biomass before fiber shives conversion is less than 75%.

15. The process of claim 1, wherein the steam exploded ligno-cellulosic biomass before fiber shives conversion has a dry matter content of at least 20% by weight of the total content of the steam exploded ligno-cellulosic biomass before fiber shives conversion.

16. The process of claim 1, wherein the dry matter content of the steam exploded ligno-cellulosic biomass before fiber shives conversion is a range of 25% by weight of the total content of the steam exploded ligno-cellulosic biomass before fiber shives conversion to less than 80% by weight of the total content of the steam exploded ligno-cellulosic biomass after fiber shives conversion.

17. The process of claim 1, further comprising dispersing an amount of the steam exploded ligno-cellulosic biomass before, during or after fiber shives conversion into an amount of a liquid carrier comprising water to create a slurry stream.

18. The process of claim 17, wherein the slurry stream has a viscosity less than 10 Pa s, wherein the viscosity is measured at 25° C., at a shear rate of 10 $s^{-1}$ and at a dry matter content of 7% by weight of the slurry stream.

19. The process of claim 17, wherein the slurry stream has a dry matter content less than 100% but greater than 5%.

20. The process of claim 17, wherein the slurry stream does not contain ionic groups derived from added mineral acids, mineral bases, organic acids, or organic bases.

* * * * *